(12) United States Patent
Kurokawa et al.

(10) Patent No.: US 6,996,499 B2
(45) Date of Patent: Feb. 7, 2006

(54) ABNORMALITY DETECTING DEVICE FOR GAS SENSOR

(75) Inventors: Eiichi Kurokawa, Okazaki (JP); Tomoo Kawase, Aichi-ken (JP)

(73) Assignee: DENSO Corporation, Kariya (JP)

( * ) Notice: Subject to any disclaimer, the term of this patent is extended or adjusted under 35 U.S.C. 154(b) by 5 days.

(21) Appl. No.: 10/645,562

(22) Filed: Aug. 22, 2003

(65) Prior Publication Data

US 2004/0153258 A1 Aug. 5, 2004

(30) Foreign Application Priority Data

Aug. 29, 2002 (JP) ............................. 2002-251714
May 29, 2003 (JP) ............................. 2003-152815

(51) Int. Cl.
*G06F 11/30* (2006.01)
*G01N 27/26* (2006.01)

(52) U.S. Cl. ...................... 702/185; 702/183; 204/401

(58) Field of Classification Search ................ 702/185, 702/184, 183, 182, 35; 204/401, 425, 427, 204/406; 205/775
See application file for complete search history.

(56) References Cited

U.S. PATENT DOCUMENTS 5,558,752 A * 9/1996 Wang et al. ................. 204/401
5,709,198 A 1/1998 Sagisaka et al.
6,096,186 A * 8/2000 Warburton ................... 205/782
6,164,125 A 12/2000 Kawase et al.

FOREIGN PATENT DOCUMENTS

| JP | 8-271475 | 10/1996 |
| JP | 11-6812 | 1/1999 |
| JP | 2002-202285 | 7/2002 |

* cited by examiner

*Primary Examiner*—Bryan Bui
*Assistant Examiner*—Meagan S Walling
(74) *Attorney, Agent, or Firm*—Nixon & Vanderhye P.C.

(57) ABSTRACT

In a device for detecting an abnormality of a gas sensor having a detected cell in which a pair of electrodes are provided on a solid electrolyte material, a microcomputer temporarily inputs a test signal including an alternating current component to a signal line connected to the electrode and detects a response signal developing in response to the test signal. If there is no disconnection in the cell, a current corresponding to the alternating current component flows between the electrodes due to a parasitic capacity of the cell to produce the response signal. If there is a disconnection therein, the magnitude of the response signal becomes zero. Therefore, if a detection value of the response signal falls below a reference value, a decision is made that a disconnection abnormality occurs in the cell. This enables a disconnection in the gas sensor to be detected with accuracy.

16 Claims, 20 Drawing Sheets

ABNORMALITY DETECTING DEVICE FOR GAS SENSOR

BACKGROUND

1) Technical Field

The present exemplary embodiments relate to a device for detecting an abnormality or failure of a gas sensor.

2) Description of the Related Art

Gas sensors have been employed in various fields. For example, a gas sensor is provided in an exhaust pipe of an internal combustion engine to detect a gas concentration such as a concentration of oxygen of an exhaust gas emitted from the internal combustion engine body so that the detection signal is used for the control of parts of the engine body.

In general, a gas sensor for internal combustion engines is recently made of an oxygen ionic conductive solid electrolyte material such as zirconia. For example, there has been known a gas sensor designed such that a chamber is formed to take oxygen in and out between the exterior of the gas sensor in which a gas to be measured exists and the interior of the gas sensor and the oxygen is introduced/ejected into/from the chamber through the use of a cell having a pair of electrodes on its solid electrolyte material (member). In this gas sensor, a voltage is applied between the pair of electrodes through signal lines connected thereto to move (pump) oxygen ions serving as a carrier in the interior of the solid electrolyte material to take oxygen in and out. Moreover, a limiting current corresponding to the oxygen concentration in the interior of the chamber is applied between the electrodes to detect a current flowing through the signal lines for detecting the oxygen concentration. In addition, there has been known a gas sensor in which a plurality of cells each having such a construction are provided to detect NOx, CO and HC additionally.

Meanwhile, in the recent years, in internal combustion engines and others, the presence or absence of various types of abnormalities are self-diagnosable in working conditions or the like. Japanese Patent Laid-Open No. HEI 11-6812 discloses an apparatus for making a decision on the occurrence of a trouble of a gas sensor. In particular, this apparatus is designed to make a decision on a current-carrying failure of a heater built in the gas sensor, and a decision is made as to the presence or absence of malfunction or abnormality such as disconnection or breakage by, when the heater is energized, making binary judgment on a voltage or current on the basis of its magnitude.

Accordingly, it is desirable that a disconnection between the cell electrodes and the signal lines or in the middle of the signal lines is detected through the use of the technique disclosed in the above-mentioned document to quickly make a decision as to a state of difficulty being encountered in achieving the normal detection of gas concentration. For example, it is considered that a voltage is applied between the electrodes of the cell to detect the presence or absence of a current.

However, the trend in the gas sensor is toward the size reduction and multi-cell construction, and the occurrence or non-occurrence of disconnection is not always detectable with accuracy on the basis of the current detection. This is due to the interference with a heater or cell integrated therewith.

SUMMARY OF THE PRESENT EXEMPLARY EMBODIMENTS

The present exemplary embodiments have been made in consideration of this situation, and it is therefore an object of the invention to provide a gas sensor abnormality detecting device capable of accurately detecting the presence or absence of disconnection in a gas sensor.

For this purpose, in accordance with a first aspect of a present exemplary embodiment, there is provided a gas sensor abnormality detecting device made to detect the presence or absence of abnormality of a gas sensor having a cell in which a pair of electrodes are formed on a solid electrolyte material to output a signal corresponding to a composition of a measured gas on surfaces of the electrodes through signal lines connected to the electrodes, the device comprising signal inputting means for temporarily inputting a test signal including an alternating-current component through the signal line to the cell undergoing abnormality detection, response signal detecting means for detecting a response signal developing in the signal line in response to the inputting of the test signal, and decision means for comparing a detection value of the response signal with a prescribed value and, if the detection value resides in one of regions defined by the prescribed value, making a decision that disconnection abnormality occurs in the cell undergoing the abnormality detection.

Since the cell electrodes have a two-dimensional spread to secure a quantity of oxygen for the movement in a solid electrolyte material, the equivalent circuit of the cell has a relatively large parasitic capacity. Therefore, the impedance for an alternating-current component is extremely lower as compared with the impedance in a disconnection portion when a disconnection abnormality occurs in the cell. Accordingly, the response signal varies largely in accordance with the presence or absence of a disconnection. This enables clear discrimination from a signal of a current flowing in the signal line in a steady state due to the interference with the other cells or the like, which enhances the decision accuracy.

In addition, since the response signal varies largely in accordance with the presence or absence of disconnection, if the temperature of the solid electrolyte material rises in some degree and the impedance thereof decreases to some extent, the disconnection detection becomes promptly feasible.

According to second aspect of a present exemplary embodiment, in the above-mentioned configuration, for the detection of the response signal, a predetermined time delay is set with respect to test signal.

In the case of a size-reduced or multi-cell gas sensor, for example, when the electrodes of a plurality of cells are formed on the same solid electrolyte material, a cell undergoing detection and other cells are brought close to each other and, hence, a parasitic capacity exists between the cells. Accordingly, even if disconnection occurs in one electrode, in response to a test signal, a current flows through a parasitic capacity between the electrode in which no disconnection occurs and an electrode of the other cell. For this reason, for the detection of a response signal, a predetermined time delay is set with respect to a test signal to make the detection on disconnection in a state where the influence of the parasitic capacity between the cells on a signal on the signal line decreases, thereby enhancing the accuracy of the disconnection detection.

Furthermore, in accordance with a third aspect of a present exemplary embodiment, there is provided a gas sensor abnormality detecting device made to detect the presence or absence of abnormality of a gas sensor composed of a plurality of cells each having a pair of electrodes formed on a solid electrolyte material to output a gas detection signal corresponding to a composition of a measured gas on surfaces of the electrodes through signal lines connected to the electrodes and made such that one electrodes of the pairs of electrodes of the plurality of cells are placed to confront a common chamber, the device comprising test signal inputting means for temporarily inputting a test signal including an alternating-current component through the signal line to a specified cell of the plurality of cells, response signal detecting means for, in response to the inputting of the test signal, detecting a response signal developing in the signal line for a cell, undergoing abnormality detection, other than the specified cell, and decision means for comparing a detection value of the response signal with a prescribed value and, if the detection value resides in preset one of regions defined by the prescribed value, making a decision that disconnection abnormality occurs in the cell undergoing the abnormality detection.

In the case of a size-reduced or multi-cell gas sensor, for example, when the electrodes of a plurality of cells are formed on the same solid electrolyte material, a cell undergoing detection and other cells are brought close to each other and, hence, a parasitic capacity exists between the cells. Therefore, the impedance for an alternating-current component is extremely lower as compared with the impedance in a disconnected portion when disconnection abnormality occurs in a cell so that a response signal varies largely in accordance with the occurrence or non-occurrence of the disconnection. This enables clear discrimination from a signal of a current flowing in the signal lines in a steady state due to the interference with the other cells or the like, which enhances the decision accuracy.

Moreover, in a case in which the test signal output term can be prolonged to make the disconnection detection in sufficient time, when a test signal is inputted to a specified cell, the oxygen concentration in the chamber the electrode of the specified cell confronts varies through an action of pumping oxygen in and out. Therefore, if no disconnection occurs in signal lines connected to the electrode of the cell to be detected, confronting the same chamber, the gas detection signal varies in accordance with the oxygen concentration variation, which produces a response signal. This enables the detection of the presence or absence of disconnection. Since the response signal is based upon the actual variation of oxygen concentration in the chamber, it is possible to make clear discrimination from a signal of a current flowing in the signal line in a steady state due to the interference with the other cells or the like, which enhances the decision accuracy.

Still moreover, since a test signal inputting means is not provided with respect to the cell undergoing the detection, the degree of freedom of design increases.

According to a fourth aspect of a present exemplary embodiment, the above-mentioned device according to the third aspect further comprises second response signal detecting means for, in response to the test signal with respect to the specified cell, detecting a response signal developing in a signal line for the specified cell, and second decision means for comparing a detection value of the response signal with a prescribed value to, if the detection value resides in preset one of the regions defined by the prescribed value, make a decision that disconnection abnormality occurs in the specified cell.

In this case, the test signal for disconnection abnormality decision on the specified cell can also be used for the disconnection detection of the cell being detected, which leads to simplifying the configuration.

According to a fifth aspect of a present exemplary embodiment, the above-mentioned device according to the fourth aspect further comprises response signal detecting means for, in response to the inputting of the test signal to the specified cell, detecting a response signal developing in a signal line for the specified cell, impedance calculating means for obtaining an impedance between the electrodes of the specified cell on the basis of the test signal and the response signal, and heater control means for controlling a heater integrated with gas sensor together with the cell on the basis of the obtained impedance.

In this case, the test signal for the impedance detection for the heater control can also be used for the disconnection detection on the cell to be detected, which simplifies the configuration.

According to a sixth aspect of a present exemplary embodiment, the above-mentioned device further comprises temperature state detecting means for detecting a temperature state of the solid electrolyte material and inhibiting means for inhibiting the abnormality decision processing in the decision means until the temperature state reaches a predetermined temperature region of the solid electrolyte material.

In the case of the solid electrolyte material being in a cool condition, the impedance between the electrodes is high and the parasitic capacity is low. When the disconnection detection is made in this condition, difficulty is encountered in obtaining a response signal having a sufficient magnitude. For this reason, the abnormality decision is made after the temperature state of the solid electrolyte material reaches a predetermined temperature region thereof, thereby enhancing the disconnection decision accuracy.

According to a seventh aspect of a present exemplary embodiment, in the above-mentioned device according to the sixth aspect, the temperature state detecting means obtains the impedance between the electrodes on the basis of the test signal and the response signal, with the impedance being a parameter in the temperature state.

Since the impedance between the electrodes decreases as the temperature state of the solid electrolyte material rises toward the activating temperature region, it is possible to properly seize the temperature state of the solid electrolyte material on the basis of the inter-electrode impedance. Moreover, there is no need to use sensors additionally, which simplifies the configuration.

According to an eighth aspect of a present exemplary embodiment, in the above-mentioned device, the test signal inputting means inputs a temporary voltage variation as the test signal to the signal line, and the response signal detecting means detects a variation of a current flowing through the signal line as the response signal, and the decision means sets the preset one region as a smaller region than the prescribed value and, when the detection value falls below the prescribed value, makes a decision that disconnection abnormality occurs in the cell forming the abnormality-detected object.

In a case in which an alternating voltage is applied as the test signal to make the disconnection detection on the basis of a current variation, due to the aforesaid parasitic capacity, an alternating current flows between the electrodes if the disconnection does not occur in the signal lines connected to the electrodes, and the current response signal stemming from this alternating current becomes relatively high in magnitude. On the other hand, in the case of the occurrence of disconnection, the alternating current becomes substantially zero. Therefore, when the one region is set in a smaller region than the prescribed value, the decision on disconnection is feasible.

According to a ninth aspect of a present exemplary embodiment, in the above-mentioned device, the test signal inputting means inputs a temporary voltage variation as the test signal to the signal line, and the response signal detecting means detects a variation of a voltage in the signal line as the response signal, and the decision means sets the preset one region as a larger region than the prescribed value and, when the detection value exceeds the prescribed value, makes a decision that disconnection abnormality occurs in the cell forming the abnormality-detected object.

In a case in which an alternating voltage is applied as the test signal to make the disconnection detection on the basis of a voltage variation, due to the aforesaid parasitic capacity, an alternating current flows between the electrodes if the disconnection does not occur in the signal lines connected to the electrodes. Since the impedance for an alternating current component in a cell is low as mentioned above, the voltage response signal stemming from this alternating current becomes relatively low in magnitude. Because the impedance in the cell is low, if disconnection occurs, the voltage response signal becomes high due to the impedance at the disconnected portion. Therefore, when the one region is set in a larger region than the prescribed value, the decision on disconnection is feasible.

In addition, in accordance with a tenth aspect of a present exemplary embodiment, there is provided a gas sensor abnormality detecting device made to detect the presence or absence of abnormality of a gas sensor composed of a cell having a pair of electrodes formed on a solid electrolyte material to output a gas detection signal corresponding to a composition of a measured gas on surfaces of the electrodes through signal lines connected to the electrodes, the device comprising test signal inputting means for temporarily inputting a test signal including an alternating-current component through the signal line with respect to a cell undergoing abnormality detection, response signal detecting means for, in response to the inputting of the test signal, detecting a response signal developing in the signal line, impedance calculating means for obtaining an impedance between the electrodes on the basis of the test signal and the response signal, and decision means for comparing the obtained impedance value with a prescribed value and, if the obtained impedance value exceeds the prescribed value, making a decision that disconnection abnormality occurs in the abnormality-detected cell.

Since the electrodes of a cell have a two-dimensional spread to secure a quantity of oxygen moving in the solid electrolyte material, the equivalent circuit of the cell has a relatively large parasitic capacity. Accordingly, when disconnection abnormality occurs in a cell, the impedance for the alternating current component is extremely lower as compared with the impedance in the disconnected portion. Therefore, the impedance or the response signal varies largely in accordance with the presence or absence of disconnection. The impedance can be obtained on the basis of a voltage variation or current variation serving as a test signal and a current variation or voltage variation serving as a response signal. Since the response signal shows a large difference as mentioned above, in making a decision on disconnection on the basis of an impedance based thereon, the effect of a signal of a current flowing through a signal line due to the interference with other cells or the like is minute. Accordingly, a high decision accuracy is attainable.

According to an eleventh aspect of a present exemplary embodiment, the above-mentioned device according to the tenth aspect further comprises temperature state detecting means for detecting a temperature state of the solid electrolyte material and inhibiting means for inhibiting the abnormality decision processing in the decision means until the temperature state reaches a predetermined temperature region of the solid electrolyte material.

In the case of the solid electrolyte material being in a cool condition, the impedance between the electrodes is high and the parasitic capacity is low. When the disconnection detection is made in this condition, difficulty is encountered in obtaining a response signal having a sufficient magnitude. For this reason, the abnormality decision is made after the temperature state of the solid electrolyte material reaches a predetermined temperature region thereof, thereby enhancing the disconnection decision accuracy.

According to a twelfth aspect of a present exemplary embodiment, in the above-mentioned device according to the eleventh aspect, the temperature state detecting means obtains an energizing time with respect to a heater integrated with the gas sensor together with the cell, with the energizing time being a parameter in the temperature state.

In the case of the solid electrolyte material being in a cool condition, the impedance between the electrodes is high. Accordingly, even if there is no disconnection, there is a possibility of a disconnection decision being made in error. For this reason, the abnormality decision is made after the heater energizing time for heating of the solid electrolyte material becomes sufficient so that the temperature state of the solid electrolyte material reaches a predetermined temperature region of the solid electrolyte material, thereby enhancing the disconnection decision accuracy.

According to a thirteenth aspect of a present exemplary embodiment, in the above-mentioned device according to the eleventh aspect, the temperature state detecting means obtains a total applied electric energy to a heater integrated with the gas sensor together with the cell, with the total applied electric energy being a parameter in the temperature state.

In the case of the solid electrolyte material being in a cool condition, the impedance between the electrodes is high. Accordingly, even if no disconnection occurs, there is a possibility of a disconnection decision being made in error. For this reason, the abnormality decision is made after the total applied electric energy to the heater for heating of the solid electrolyte material becomes sufficient so that the temperature state of the solid electrolyte material reaches a predetermined temperature region of the solid electrolyte material, thereby enhancing the disconnection decision accuracy.

According to a fourteenth aspect of a present exemplary embodiment, in the above-mentioned device, the aforesaid test signal inputting means constitutes a power supply of the cell and temporarily inputs a voltage variation or a current variation to the signal line, and the response signal detecting means detects a variation of current flowing through the signal line or a voltage variation between the electrodes as the response signal.

In this case, the test signal is generated by changing the voltage or current from the cell power supply, thereby eliminating the need for the additional employment of a signal generating source, which leads to simplifying the configuration.

According to a fifteenth aspect of a present exemplary embodiment, in the above-mentioned device according to the fourteenth aspect, the test signal inputting means inputs a voltage or current varying in both a positive and negative directions with respect to a voltage or current immediately before.

In this case, even if the charging state of the cell parasitic capacity varies due to a voltage variation, the charging state is quickly restored to its original state due to the variation of the voltage in the opposite direction. Thus, the normal gas concentration detection becomes promptly feasible without waiting for the natural discharge depending upon the time constant of a circuit including the cell.

According to a sixteenth aspect of a present exemplary embodiment, in the above-mentioned device according to the fourteenth aspect, the test signal inputting means inputs a voltage or current varying in one of a positive and negative directions with respect to a voltage or current immediately before.

In this case, since the voltage or current is not varied in the opposite direction with respect to the voltage or current immediately before, the configuration becomes simple.

BRIEF DESCRIPTION OF THE DRAWINGS

Other objects and features of a present exemplary embodiment will become more readily apparent from the following detailed description of the preferred embodiments taken in conjunction with the accompanying drawings in which.

DESCRIPTION OF THE PREFERRED EMBODIMENTS

Figure 1:
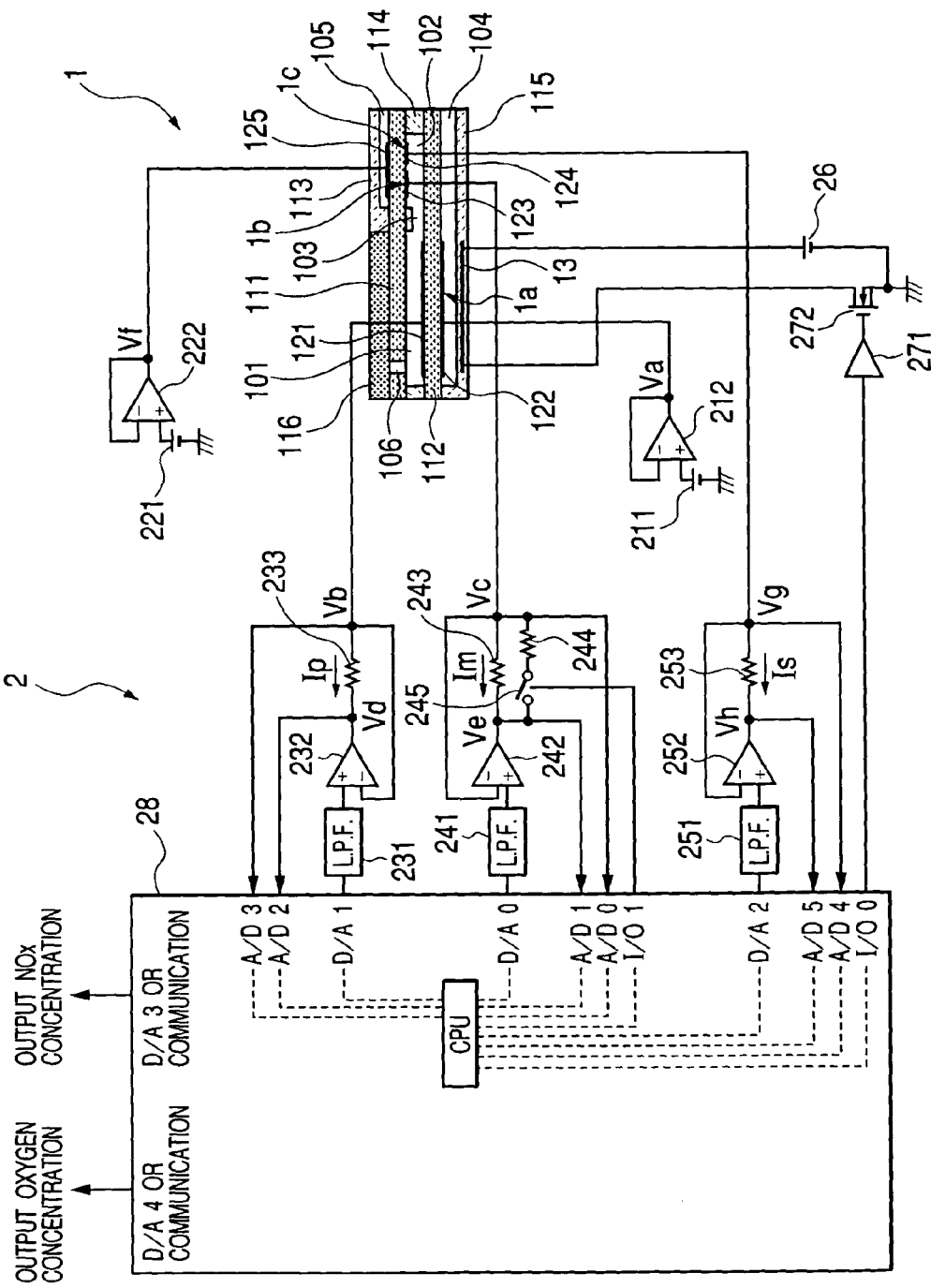
FIG. 1 is an illustration of a configuration of a gas concentration detecting apparatus employing an abnormality detecting device for a gas sensor according to a present exemplary embodiment.

FIG. 1 is an illustration of a gas concentration detecting apparatus employing an abnormality detecting device for a gas sensor according to a present exemplary embodiment. In this embodiment, the gas concentration detecting apparatus is for use in, for example, an internal combustion engine of a vehicle.

A gas sensor, generally designated at reference numeral 1, is placed in an exhaust pipe through which an exhaust gas emitted from an engine flows, and is connected through a wiring cable to a control circuit generally denoted at reference numeral 2. A microcomputer 28 constituting the control circuit 2 conducts calculating operations on oxygen concentration and NOx concentration (which will hereinafter be referred to equally as "gas concentration") on the basis of signals from the gas sensor 1 and outputs the calculation results.

Figure 2:
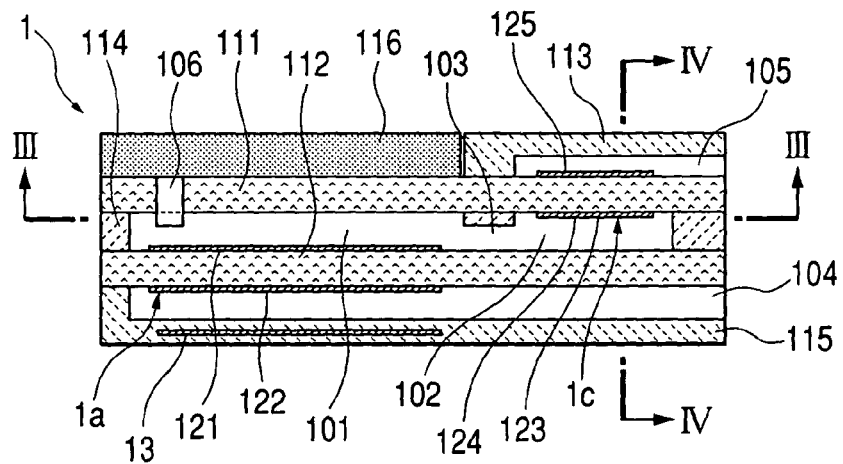
FIG. 2 is a cross-sectional view showing an essential part of the gas sensor.
Figure 3:
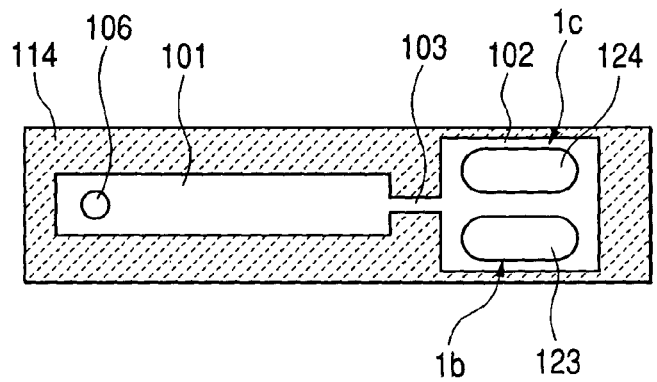
FIG. 3 is a cross-sectional view taken along a line III—III of FIG. 2.
Figure 4:
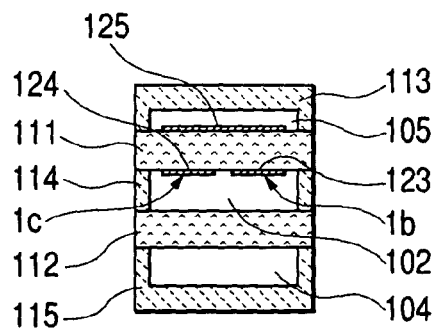
FIG. 4 is a cross-sectional view taken along a line IV—IV of FIG. 2.

As shown in FIGS. 2, 3 and 4, the gas sensor 1 is constructed by stacking solid electrolyte layers 111 and 112 each made of an oxygen ionic conductive solid electrolyte material such as zirconia, insulating layers 113 and 114 made of an insulating material such as alumina, a layer 115 made of an insulating material such as alumina or a solid electrolyte material such as zirconia, and others in thickness directions, and has an elongated configuration in a longitudinal direction as a whole. The insulating layer 114 interposed between the solid electrolyte layers 111 and 112 is partially punched in a thickness direction to form two chambers 101 and 102 residing between the solid electrolyte layers 111 and 112 and communicating through an area reduction portion 103 with each other. The chambers 101 and 102 are located in a longitudinal direction, and the second chamber 102 on the proximal side of the gas sensor 1 has a width approaching twice that of the first chamber 101 on the tip side of the gas sensor 1.

Air ducts 104 and 105, using the solid electrolyte layers 111 and 112 partially as duct walls, are formed on the opposite side to the chambers 101 and 102 in a state where the solid electrolyte layers 111 and 112 are interposed therebetween. The air ducts 104 and 105 are opened to the atmosphere on the proximal side of the gas sensor 1. The first air duct 104 extends to confront the first chamber 101 in a state where the solid electrolyte layer 112 is interposed therebetween, while the second air duct 105 extends to confront the second chamber 102 in a state where the solid electrolyte layer 111 is interposed therebetween. In a case in which the gas sensor 1 is used for an internal combustion engine, the gas sensor 1, together with a holder member for holding the gas sensor 1 and others, is placed to penetrate a pipe wall of an exhaust pipe, and the air ducts 104 and 105 communicate with the exterior of the exhaust pipe and form a reference oxygen concentration space.

In FIG. 2, at the position of the first chamber 101, a pinhole 106 is made in the upper side solid electrolyte layer 111 to penetrate it in a thickness direction, and an exhaust gas around the gas sensor 1 is introduced through the pinhole 106 into the interior of the first chamber 101. The opening end of the pinhole 106 is covered with a porous diffusion layer 116 such as porous alumina to prevent the invasion of fine exhaust particles into the interior of the chamber 101.

At the position of the first chamber 101, a pair of electrodes 121 and 122 are formed on upper and lower surfaces of the solid electrolyte layer 112 to be in opposed relation to each other in a state where the solid electrolyte layer 112 is interposed therebetween, and the solid electrolyte 112 and the electrodes 121 and 122 organize a pump cell 1a. Of the electrodes 121 and 122 organizing the pump cell 1a, the electrode 121 facing the chamber 101 is made of a noble metal such as Au—Pt inactive for decomposition (reduction) of NOx. In the following description, the electrode 121 confronting the chamber 101 will hereinafter be referred to equally as a "chamber side pump electrode 121", while the electrode 122 confronting the air duct 104 will hereinafter be referred to equally as an "air side pump electrode 122".

At the position of the second chamber 102, two pairs of electrodes 123, 125 and 124, 125 are formed on upper and lower surfaces of the solid electrolyte layer 111 in a state where the solid electrolyte layer 112 is interposed therebetween, with the electrodes 125, 125 confronting the air duct 105 being formed as a common electrode. The solid electrolyte layer 111 and the electrodes 123 and 125 constitute a monitor cell 1b. Moreover, the solid electrolyte layer 111 and the electrodes 124 and 125 constitute a sensor cell 1c. Of the electrodes 123 and 124 confronting the chamber 102, the electrode 123 of the monitor cell 1b is made of a noble metal such as Au—Pt inactive for the decomposition (reduction) of NOx, while the electrode 124 of the sensor cell 1c is made of a noble metal such as Pt active for the decomposition (reduction) of NOx. In the following description, the electrode 123 of the monitor cell 1b confronting the chamber 102 will hereinafter be referred to equally as a "chamber side monitor electrode 123", while the electrode 124 of the sensor cell 1c confronting the chamber 102 will hereinafter be referred to equally as a "chamber side sensor electrode 124". Moreover, the electrode 125 formed in common to the monitor cell 1b and the sensor cell 1c and confronting the air duct 106 will hereinafter be referred to equally as an "air side sensor/monitor electrode 125".

In addition, a line pattern such as Pt is buried in the layer 115 forming a duct wall together with the solid electrolyte layer 112 to make a heater 13 for heating the entire gas sensor 1. The heater 13 is of an electrical type which generates joule heat when energized.

In the gas sensor 1, an exhaust gas flowing around the gas sensor 1 passes through the porous diffusion layer 116 and the pinhole 106 and enters the first chamber 101, and when a voltage is applied between the electrodes 121 and 122 of the pump cell 1a in a state where the air side pump electrode 122 side is made positive, oxygen of the exhaust gas is decomposed at the chamber side pump electrode 122 and ionized, and then ejected through the solid electrolyte layer 111 to the air duct 104. At this time, the flowing of oxygen into the interior of the first chamber 101 depends upon the passing resistances of the pinhole 106 and the porous diffusion layer 116. If the applied voltage between the electrodes 121 and 122 of the pump cell 1a is set in a limiting current region, the oxygen concentration of the exhaust gas is detectable on the basis of the value of a current flowing at that time. Since the chamber side pump electrode 121 is inactive for the decomposition of NOx, NOx remains in the interior of the first chamber 101.

Since the exhaust gas diffuses from the first chamber 101 through the area reduction portion 103 to the second chamber 102, the exhaust gas in which the oxygen concentration lowers exists in the second chamber 102. When a voltage is applied between the electrodes 123 and 125 of the monitor cell 1b and between the electrodes 124 and 125 of the sensor cell 1c in a state where the air side sensor/monitor electrode 125 side is made positive, in the cells 1b and 1c, a limiting current flows because the excess oxygen in the interior of the chamber 102 is discharged to the air duct 105. In this case, of the electrodes 123 and 124 confronting the second chamber 102, only the chamber side sensor electrode 124 is active for the decomposition of NOx and, hence, the current flowing in the sensor cell 1c is more than the current flowing in the monitor cell 1b by an amount corresponding to the oxygen ions developing due to the decomposition of NOx at the chamber side sensor electrode 124. Accordingly, the NOx concentration of the exhaust gas is detectable on the basis of the difference between the current flowing in the monitor cell 1b and the current flowing in the sensor cell 1c.

Secondly, a decision will be given hereinbelow of an electrical arrangement of the gas concentration detecting apparatus.

The control circuit 2 comprises a general microcomputer 28 including a CPU, A/D converters (A/D 0 to A/D 5), D/A converters (D/A 0 to D/A 4), I/O ports (I/O 0, I/O 1) and others. The microcomputer 28 serves as power supply sources for the pump cell 1a and the monitor cell 1b and properly outputs instruction voltages as application voltages to the pump cell 1a and the monitor cell 1b through the D/A 1 and D/A 0. Moreover, the microcomputer 28 receives gas detection signals through the A/D 0 to A/D 5 to detecting currents flowing in the respective cells 1a to 1c, and calculates an oxygen concentration or NOx concentration of an exhaust gas on the basis of the detected currents of the cells 1a to 1c to output the calculation results through the D/A 4 and D/A 3 to the external. Still moreover, the microcomputer 28 outputs control signals through the I/O 0 and I/O 1.

Concretely, a reference voltage Va is applied from a voltage follower operational amplifier 212, which receives an output of a reference voltage source 211, to the air pump electrode 122 of the pump cell 1a, while a voltage Vb is applied from an operational amplifier 232, to which an instruction voltage from the D/A 1 of the microcomputer 28 is inputted through a low-pass filter (which will hereinafter be referred to equally as an "LPF") 231, through a current detection resistor 233 to the chamber side pump electrode 121. The voltage Vb and an output voltage Vd of the operational amplifier 232 are inputted to the A/D 3 and A/D 2 of the microcomputer 28, respectively. Thus, a voltage (Va–Vb) (which will hereinafter be referred to equally as a "pump cell voltage Vp") is applied between the electrodes 121 and 122 of the pump cell 1a and a current (which hereinafter be referred to equally as a "pump cell current") Ip flows between the electrodes 121 and 122. This is detected as a voltage drop (Vb–Vd) due to the resistor 233. For example, the aforesaid LPF 231 is constructed as a primary filter comprising a resistor and a capacitor. The waveform of an instruction voltage from the microcomputer 28, which assumes a discrete value, is attempered or properly smoothed by the LPF 231 and then inputted to the operational amplifier 232.

Likewise, detection circuits are provided with respect to the monitor cell 1b and the sensor cell 1c. That is, a reference voltage Vf is applied from a voltage follower operational amplifier 222, which receives an output of a reference voltage source 221, to the electrode 125 common to the monitor cell 1b and the sensor cell 1c. A voltage Vc is applied from an operational amplifier 242, to which an instruction voltage from the D/A 0 of the microcomputer 28 is inputted through an LPF 241, through a current detection resistor 243 to the chamber side monitor electrode 123 of the monitor cell 1b. The voltage Vc and an output voltage Ve of the operational amplifier 242 are inputted to the A/D 0 and A/D 1 of the microcomputer 28. Thus, a voltage (Vf–Vc) (which will hereinafter be referred to equally as a "monitor cell voltage Vm) is applied between the electrodes 123 and 125 of the monitor cell 1a and a current (which will hereinafter be referred to equally as a "monitor cell current) Im flows between the electrodes 123 and 125. This is detected as a voltage drop (Vc–Ve) due to the resistor 243.

On the other hand, a voltage Vg is applied from an operational amplifier 252, to which an instruction voltage from the D/A 2 of the microcomputer 28 is inputted through an LPF 251, through a current detection resistor 253 to the electrode 124 of the sensor cell 1c confronting the chamber 102. An output voltage Vh of the operational amplifier 252 and the voltage Vg are inputted through the A/D 4 and A/D 5 of the microcomputer 28 to the CPU thereof. Thus, a voltage (Vf–Vg) (which will hereinafter be referred to equally as a "sensor cell voltage Vs) is applied between the electrodes 124 and 125 of the sensor cell 1c and a current (which will hereinafter be referred to equally as a "sensor cell current") Is flows between the electrodes 124 and 125. This is detected as a voltage drop (Vg–Vh) due to the resistor 253.

In addition, the control circuit 2 is designed to detect the impedances of the cells 1a to 1c. The impedance detection is made with respect to the monitor cell 1b as a representative, and the impedance to be detected is an impedance between both the electrodes 123 and 125 (which will hereinafter be referred to equally as a "monitor impedance"). That is, at the impedance detection, the instruction voltage from the D/A 0 is varied to the positive side or negative side in a moment. This voltage variation is attempered by the LPF 241, and a sinewave-like alternating current component is included in the application voltage Vc to the chamber side monitor electrode 123 of the monitor cell 1b, i.e., the monitor cell voltage Vm. This alternating current component is preferably above 1 kHz, and the time constant of the LPF 241 is set at approximately 15 $\mu$sec. In the microcomputer 28, the impedance is obtained on the basis of a voltage variation of the monitor cell voltage Vm and a current variation of the monitor cell current Im at this time.

In this connection, another resistor 244 for the monitor cell current Im detection is provided in parallel with the resistor 243 for the monitor cell current Im detection. The resistor 244 is made to be freely switched into connected and disconnected conditions through the use of a switch 245. The switch 245 takes an open condition (off condition) or a closed condition (on condition) in accordance with a control signal from the I/O 1 of the microcomputer 28, and when it is in the on condition, the resistance value of the resistor for the monitor cell current Im detection is reducible. The reason that the resistance value of the resistor for the monitor cell current Im detection is decreased through the turning-on of the switch 245 is that the monitor current Im at the impedance detection becomes larger than that at the gas concentration detection and, hence, there is a need to avoid the unbalanced condition between the current detection voltage (Vc–Ve) at the impedance detection and the current detection voltage (Vc–Ve) at the gas concentration detection.

Furthermore, a description will be given hereinbelow of a drive system of the heater 13. The heater 13 is energized from a battery 26, and the energizing operation therefor is switched to an on or off condition through the use of a MOSFET 272. A drive signal is inputted from the I/O 0 of the microcomputer 28 through a MOSFET driver 271 to the gate of the MOSFET 272 to conduct the on/off operation. The energizing control for the heater 13 is based on PWM control which applies a voltage in a pulse-like fashion, and the adjustment of the drive current (drive power) is made by increasing or decreasing the length of pulse-on term (drive duty) within a predetermined period.

Still furthermore, a description will be given hereinbelow of a control program to be implemented in the microcomputer 28 and an operation of this gas concentration detecting apparatus. First of all, referring to FIGS. 5 and 6, a description will be given of basic control for detecting a gas concentration.

Figure 5:
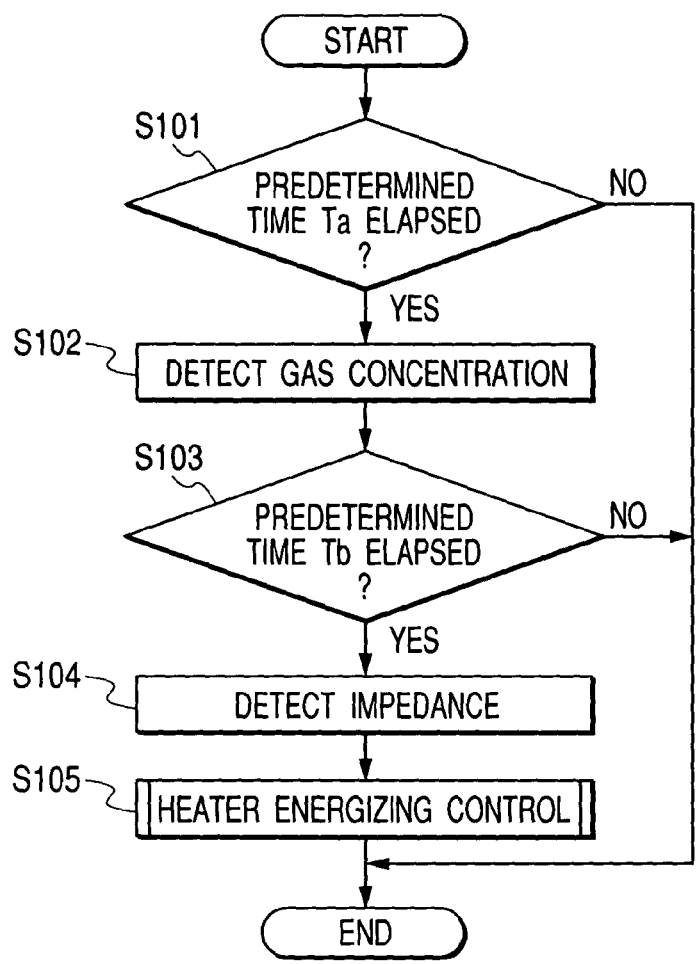
FIG. 5 is a first flow chart showing the contents of control for gas concentration detection to be implemented in a microcomputer constituting the gas concentration detecting apparatus.

FIG. 5 is the outline of a main routine, and the main routine starts in response to the control circuit 2 being powered on.

First, at a step S101, a decision is made as to whether or not a predetermined time period Ta elapses from the time of the last gas concentration detection. The predetermined time period Ta is a time corresponding to the cycle of the gas concentration detection, and for example, is set at 4 ms.

If the decision in the step S101 shows "YES", the operational flow advances to a step S102 to implement the gas concentration detection processing. In the gas concentration detection processing, an instruction voltage is set with respect to a pump cell current Ip moment to moment, and the pump cell current Ip at the output of the instruction voltage is detected. The setting of the instruction voltage is made in accordance with an applied voltage map stored in a ROM (not shown) of the microcomputer 28. Moreover, the pump cell current Ip is converted into an oxygen concentration. Still moreover, the monitor cell current Im and the sensor cell current Is are detected moment to moment, and are converted into an NOx concentration.

In the next step S103, a decision is made as to whether or nor a predetermined time period Tb elapses from the last impedance detection. The predetermined time period Tb is a time corresponding to the cycle of the impedance detection, and for example, is selectively set at 128 msec, 2 sec, etc. in accordance with an engine operating condition.

If the decision in the step S103 shows "YES", the operational flow proceeds to a step S104 to conduct the impedance detection processing, then followed by a step S105 to implement the energizing control for the heater 13 on the basis of the impedance detected in the step S104.

Figure 6:
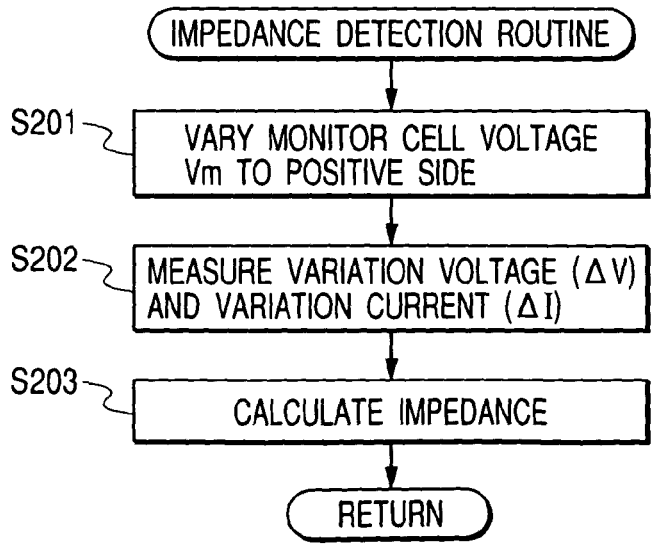
FIG. 6 is a second flow chart showing the contents of control for gas concentration detection to be implemented in a microcomputer constituting the gas concentration detecting apparatus.
Figure 7:
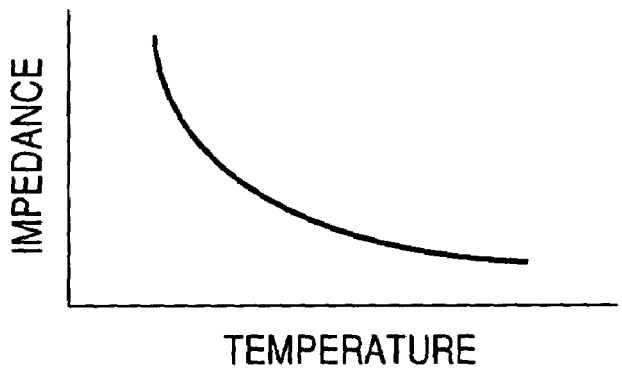
FIG. 7 is a graphic illustration useful for explaining the contents of the gas concentration detection control.

The impedance detection processing (step S104) serves as a temperature state detecting means, and as shown in FIG. 6, in a step S201, an instruction voltage from the D/A 0 is shifted to, for example, the positive side for an extremely short period of time (several tens to several hundreds μsec) to vary the monitor cell voltage Vm, and a step S202 follows to measure a variation ΔVm of the monitor cell voltage Vm and a variation ΔIm of the monitor cell current Im at that time. In this connection, before the implementation of the step S201, the resistor 244 is switched into an impedance detection mode (connected) by a signal from the I/O 1. The step S203 is the processing serving as an impedance calculating means, and the impedance is calculated on the basis of the measurement results. That is, the ratio (ΔVm/ΔIm) of the monitor cell current variation ΔIm and the monitor cell voltage variation ΔVm is calculated and is set as an impedance. The variation of the monitor cell voltage Vm is processed by the LPF 241 so as to attemper the rising and falling portions in its waveform, thereby preventing excessive spike from appearing in the monitor cell current Im due to an reactance component of the monitor cell 1b for enhancing the impedance detection accuracy. As shown in FIG. 7, this impedance shows a temperature state of the solid electrolyte layers 111 and 112 and decreases as the temperature rises. At the arrival at the solid electrolyte activating temperature region, the oxygen ions flow satisfactorily.

The heater energizing control (step S105) functions as a heater control means, and for example, until the detected impedance reaches 75% of a desired impedance, the fixed duty control is implemented, that is, the drive duty is fixed to 100%. On the other hand, if it exceeds 75% of the desired impedance, the PI control is implemented to accomplish the convergence into the desired impedance.

In addition, a description will be given hereinbelow of control for detecting disconnection of signal lines of the gas sensor 1.

(Disconnection in Pump Cell)

Figure 8:
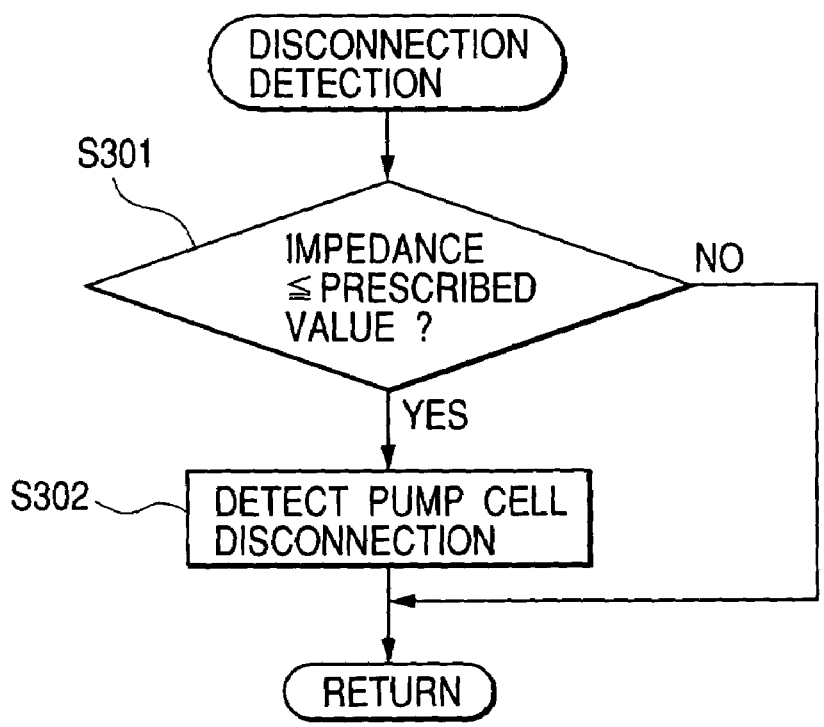
FIG. 8 is a first flow chart showing the contents of control for gas sensor abnormality detection to be implemented in the microcomputer constituting the gas concentration detecting apparatus.
Figure 9:
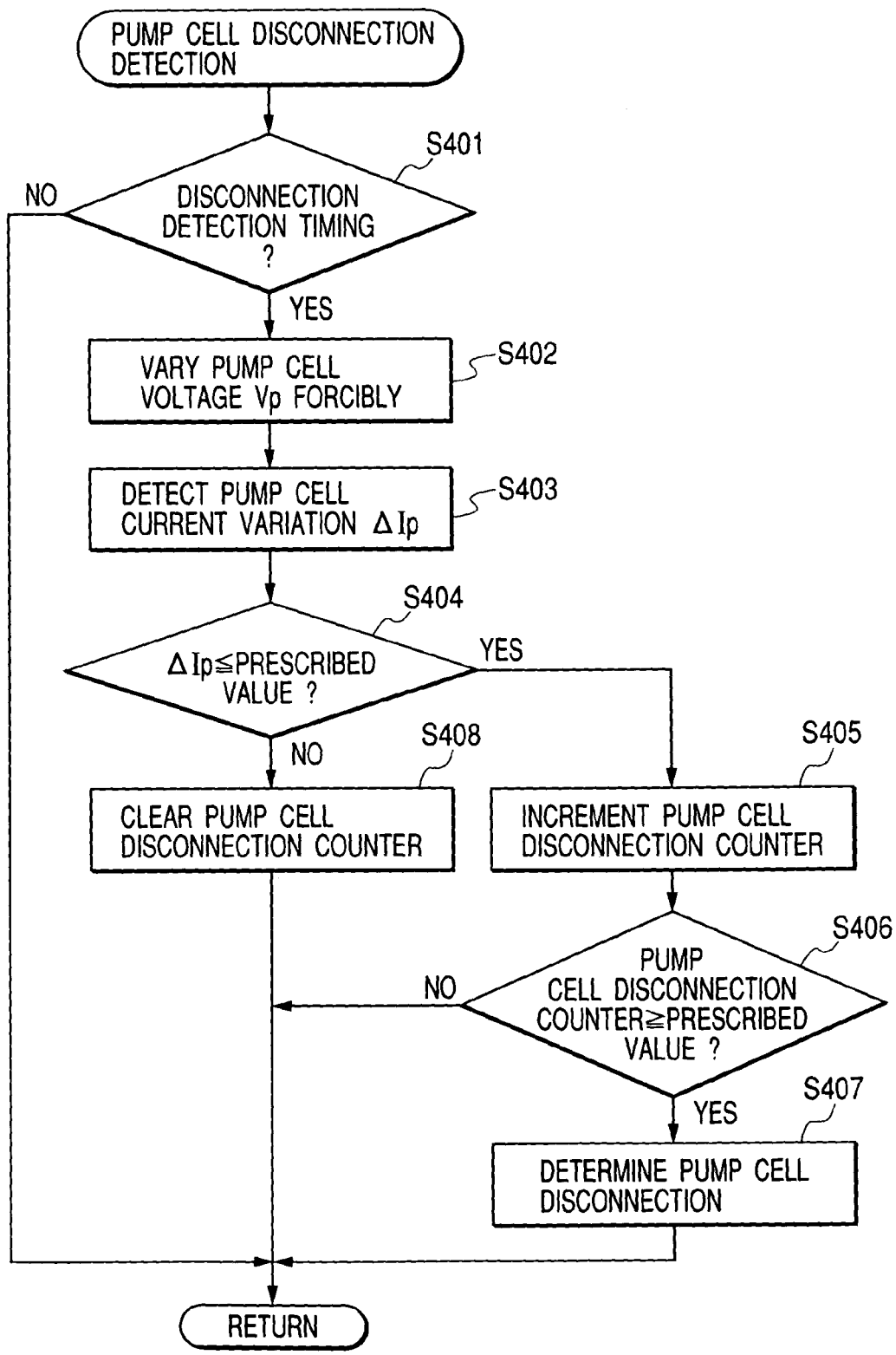
FIG. 9 is a second flow chart showing the contents of control for gas sensor abnormality detection to be implemented in the microcomputer constituting the gas concentration detecting apparatus.

FIGS. 8 and 9 shows disconnection detection processing to be implemented with respect to the pump cell 1a.

In a step S301, the impedance ZAC detected in the aforesaid impedance detection processing (step S104) is compared with a predetermined prescribed value to make a decision as to whether or not it falls below the prescribed value. The step S301 functions as an inhibiting means. If the decision in the step S301 is negative, that is, when the impedance ZAC exceeds the prescribed value, the operational flow returns. On the other hand, if the decision is affirmative, the operational flow advances to a step S302 to carry out the pump cell disconnection detection.

In the pump cell disconnection detection processing (step S302), a step S401 is first implemented to make a decision on timing of disconnection detection. If the decision in the step S401 is affirmative, the operational flow advances to a step S402. On the other hand, if the decision therein is negative, the operational flow returns. In the step S401, the affirmative decision is made every predetermined period in the microcomputer 28 to implement the step S402 and subsequent processing.

The step S402 functions as a test signal inputting means for forcing the pump cell voltage Vp to vary. An instruction voltage to be inputted from the D/A 1 to the LPF 231 is slightly shifted to the positive side with respect to the voltage value immediately before for an extremely short period of time and is then shifted from that state to the negative side with respect to the immediately-before voltage value. This produces the pump cell voltage Vp having a voltage variation shifting to the positive and negative sides with respect to the immediately-before voltage value. The variation of the instruction voltage, i.e., the variation of the pump cell voltage Vp forming a test signal, is processed by the LPF 231 to attemper the rising and falling of the waveform.

A step S403 functions as a response signal detecting means for taking in (detecting) the variation ΔIp of the pump cell current Ip forming a response signal flowing in response to the forced variation of the pump cell voltage Vp as in the case of the impedance detection processing (step S104).

Steps S404 to S408 function as a decision means, and in the step S404, the detected pump cell current variation ΔIp is compared with a preset prescribed value to make a decision as to whether if falls below the prescribed value. If the answer in the step S404 is affirmative, the operational flow advances to the step S405 to increment the pump cell disconnection counter by "1".

Figure 10:
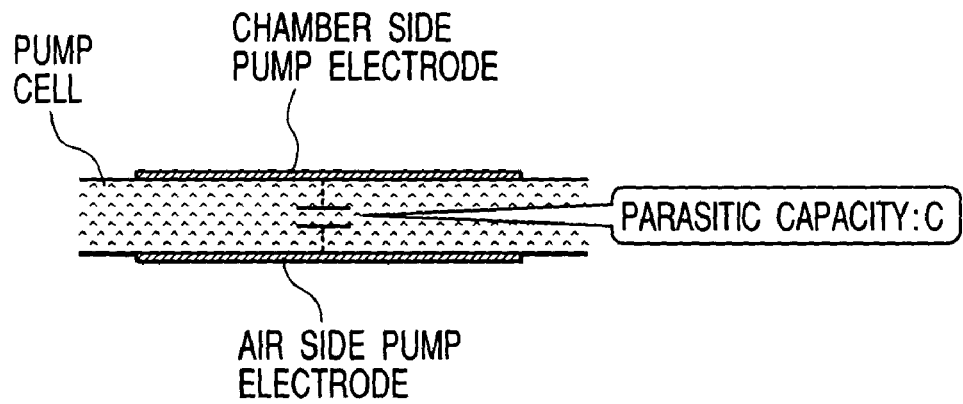
FIG. 10 shows a first cell for explaining the contents of control for gas sensor abnormality detection.
Figure 11:
FIG. 11 is an illustration of an equivalent circuit of a cell constituting the gas sensor.
Figure 12:
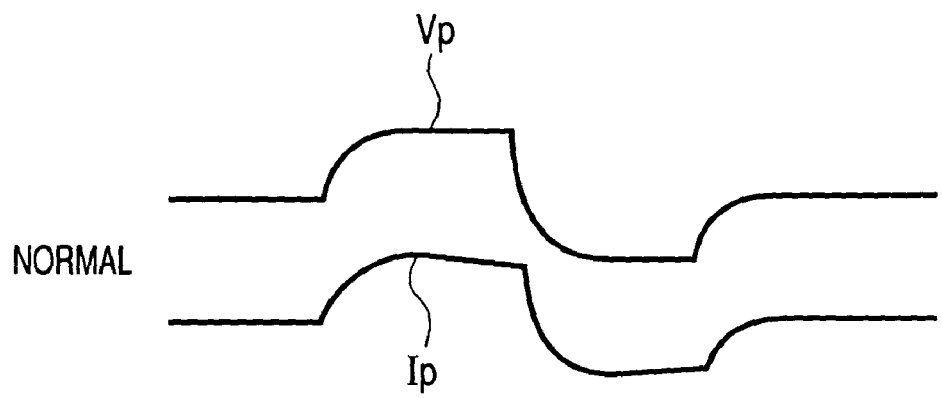
FIG. 12 is a first timing chart useful for explaining the contents of control for gas sensor abnormality detection.

In the step S404, the affirmative decision is made if a disconnection occurs in the pump cell. That is, as illustratively shown in FIG. 10, a parasitic capacity exists between the electrodes in the pump cell 1a, and the equivalent circuit of the pump cell 1a is as shown in FIG. 11. Each of the electrodes has some degree of extent for securing the quantity of oxygen moving in the solid electrolyte material, and the parasitic capacity shows a relatively large value. Therefore, the impedance component based on this parasitic capacity is extremely small. Accordingly, in response to the forced variation of the pump cell voltage Vp, if there is no disconnection in the pump cell 1a, a relatively large current variation ΔIp takes place depending on the impedance of the aforesaid equivalent circuit as shown in FIG. 12.

Figure 13:
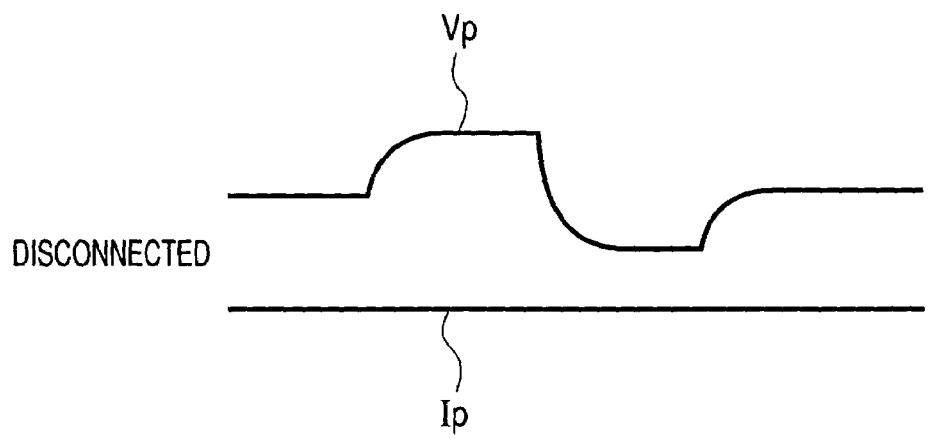
FIG. 13 is a second timing chart useful for explaining the contents of control for gas sensor abnormality detection.

On the other hand, if a disconnection occurs with respect to the electrodes 121 and 122 of the pump cell 1a, the pump cell current variation ΔIp decreases by an amount corresponding to the impedance in the disconnected portion as compared with the case of the non-occurrence of disconnection. However, since the impedance component based on the parasitic capacity is extremely small as mentioned above, the decreasing range becomes large and the pump cell current variation ΔIp does not occur substantially as shown in FIG. 13.

For this reason, if the prescribed value for the pump cell current variation ΔIp is set to a value at which the pump cell current variation ΔIp can be considered to be substantially zero, it is possible to make a decision on the presence or absence of a disconnection in the pump cell 1a.

In a present exemplary embodiment, since the pump cell voltage Vp is temporarily changed for (or within) an extremely short period of time, the resultant alternating current component produces a large pump cell current variation ΔIp through the parasitic capacity of the pump cell 1a. Even if the interference with the other cells 1b and 1c or the heater 13 integrated therewith, a fluctuation of the ground potential or the like occurs, the current variation caused by these is the degree to which the level of the pump cell current Ip varies gently. It is minute as compared with the current variation ΔIp responsive to the forced variation of the pump cell voltage Vp. Therefore, as compared with the technique of merely checking the presence or absence of a current, the decision on the presence or absence of disconnection in the pump cell 1a can be made with more accuracy. Moreover, when the parasitic capacity in the pump cell 1a reaches a level at which the pump cell current variation ΔIp is made sufficient, the disconnection detection is feasible without waiting until the solid electrolyte layers 111 and 112 reach their activating temperatures. Accordingly, it is not always required that the prescribed value for the impedance in the aforesaid step S301 be set at an impedance value corresponding to the activating temperature region, and it is can be set to be relatively higher than the impedance value corresponding to the activating temperature region. Moreover, because of the utilization of the alternating current component produced by the variation of the pump cell voltage Vp, the LPF 231 and the LPF 241 for the disconnection detection of the monitor cell 1b, which will be mentioned later, are made so as to shape the waveform to remove the spike noises, and the cut-off frequency is set in consideration of the impedance at frequency to be detected.

If the pump cell current variation ΔIp falls below the prescribed value and the pump cell disconnection counter is incremented (steps S404 and S405), in the step S406, the count value of the pump cell disconnection counter is compared with a predetermined prescribed value to make a decision as to whether or not the count value reaches the prescribed value. In the case of the negative decision, the operational flow returns. On the other hand, in the case of the affirmative decision, the step S407 follows to determine the disconnection in the pump cell 1a. For example, a flag indicative of the occurrence of pump cell disconnection is set, and the operational flow returns. Thus, in the other control such as fuel injection control, the abnormality of the gas sensor 1 becomes detectable. For example, the prescribed value for the pump cell disconnection counter is set at several times, thereby enhancing the pump cell disconnection decision accuracy.

On the other hand, if the decision in the step S404 is negative, that is, when the pump cell current variation ΔIp exceeds the prescribed value, the operational flow goes to the step S408 to clear the pump cell disconnection counter, and then returns. Therefore, the count value of the pump cell disconnection counter is incremented only when the result that the pump cell current variation ΔIp falls below the prescribed value (step S404) occurs continuously, and when the pump cell current variation ΔIp falls unexpectedly below the prescribed value, it is possible to avoid that this event is decided as the pump cell disconnection in error.

Figure 14:
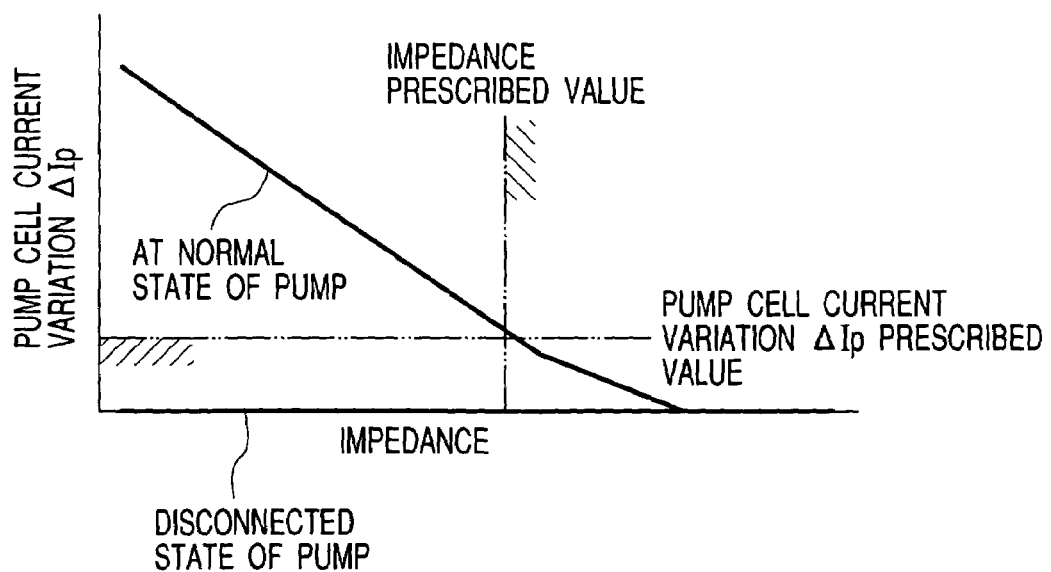
FIG. 14 is a first graphic illustration useful for the contents of control for the gas sensor abnormality detection.

Moreover, the pump cell disconnection detection processing (step S302) is conducted only when the impedance falls below the prescribed value. That is, as shown in FIG. 14, when the solid electrolyte layers 111 and 112 are low in temperature, because the impedance becomes high and the aforesaid parasitic capacity is also small, difficulty is experienced in obtaining a sufficiently large pump cell current variation ΔIp with respect to the forced variation of the pump cell voltage Vp, which leads to unclear difference from that at the occurrence of a disconnection. Moreover, there is a case in which S/N is insufficient. Therefore, the pump cell disconnection detection processing (step S302) is conducted only when the impedance falls below the prescribed value, which increases the accuracy of the decision on pump cell disconnection.

Figure 15:
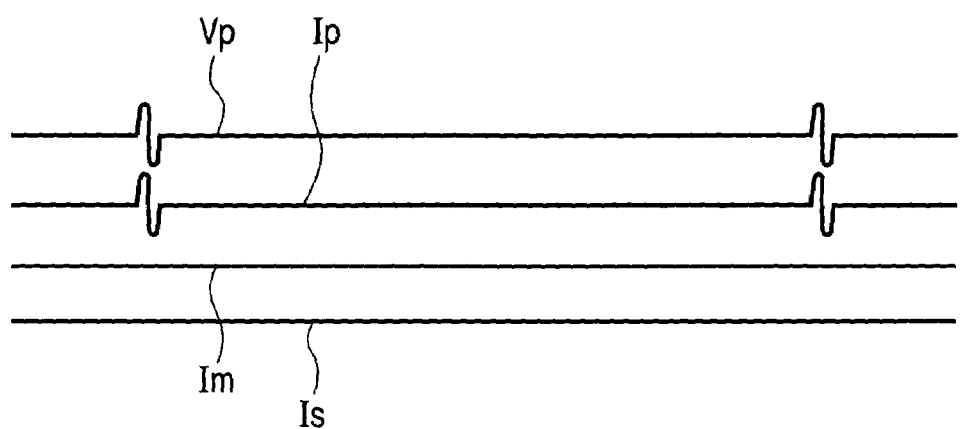
FIG. 15 is a third timing chart useful for explaining the contents of control for gas sensor abnormality detection.
Figure 16:
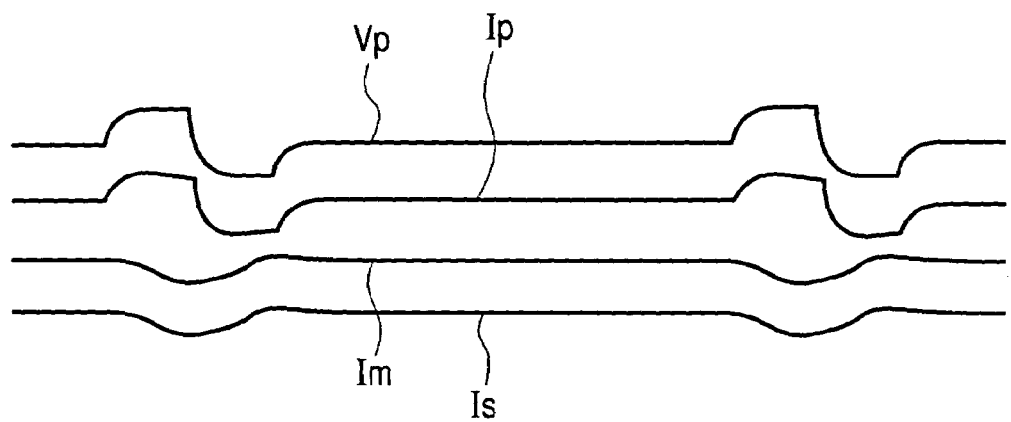
FIG. 16 is a fourth timing chart useful for explaining the contents of control for gas sensor abnormality detection.

Still moreover, in producing the forced variation of the pump cell voltage Vp (step S402), it is preferable that the time of the voltage variation is set to an extremely short period of time. FIG. 15 shows a pump cell voltage Vp, a pump cell current Ip, a monitor cell current Im and a sensor cell current Is in a case in which it is set to an extremely short period of time, while FIG. 16 shows the same in the case of a long period of time. When it is set to a long period of time, as with the gas concentration detection processing (step S1102), as in a case in which the pump cell voltage Vp is adjusted in accordance with the pump cell current Ip, there is a tendency that the pump cell voltage Vp varies statically. Thus, the oxygen concentrations in the interiors of the chambers 101 and 102 vary and the monitor cell current Im and the sensor cell current Is vary, which affects the accuracy of detection of the NOx concentration. On the other hand, if the forced variation of the pump cell voltage Vp is made for an extremely short period of time, the oxygen concentrations in the interiors of the chambers 101 and 102 do not vary substantially and, hence, there is no influence on the NOx concentration detection accuracy.

In this case, the response time at which the oxygen concentration starts to vary with respect to the forced variation of the pump cell voltage Vp depends upon the passing resistances of the pinhole 106 and the porous diffusion layer 116, and it is preferable that the time of the forced variation of the pump cell voltage Vp is set in consideration of these factors.

Figure 17:
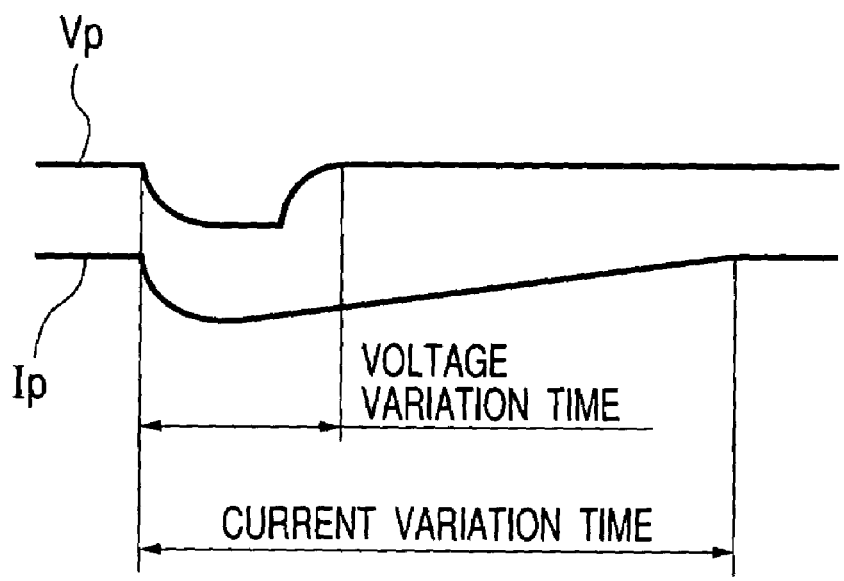
FIG. 17 is a fifth timing chart useful for explaining the contents of control for gas sensor abnormality detection.
Figure 18:
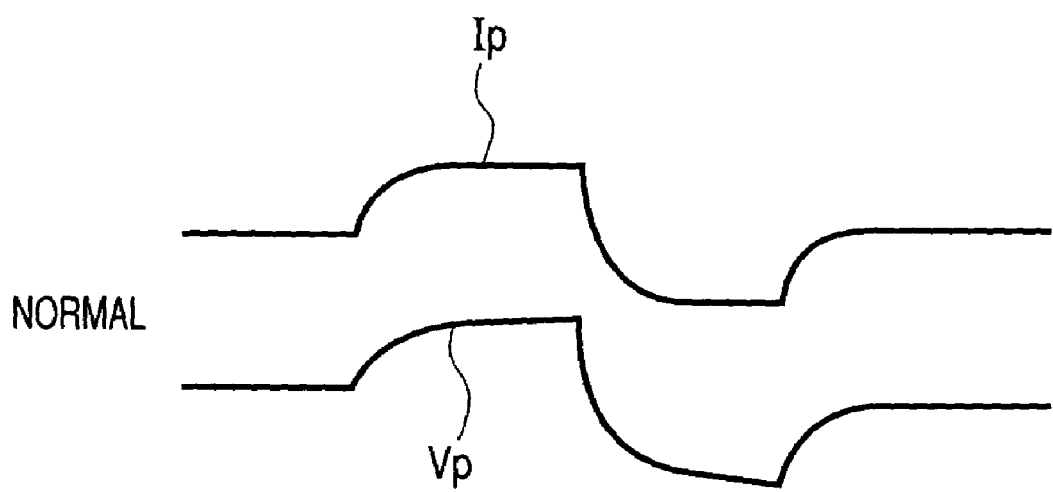
FIG. 18 is a first timing chart useful for explaining the contents of control for gas sensor abnormality detection according to a modification of the embodiment.

In addition, in this embodiment, the pump cell voltage Vp is varied successively to the positive and negative sides and, hence, the following effects are obtainable, as compared with the case in which it is varied in only one of the position direction and the negative direction. That is, as shown in FIG. 17, when the pump cell voltage Vp is varied in only one of the positive direction and the negative direction, the discharge of the electric charge made depending on the parasitic capacity of the pump cell 1a in response to the voltage variation depends on the time constant of a circuit including the pump cell 1a and, during the discharge, an error resides in the pump cell current Ip forming an oxygen concentration detection signal.

On the other hand, in the case of the voltage variation of the pump cell voltage Vp according to this embodiment, since the voltage is shifted in one direction and then shifted in the direction opposite to the first shifting direction with respect to the voltage value immediately before the voltage variation, the charging of the parasitic capacity caused by the first voltage shifting is quickly removed by the opposite-direction voltage shifting, thereby returning quickly to the normal gas concentration detection condition.

Naturally, a present exemplary embodiment includes that the forced variation of the pump cell voltage Vp takes place in one direction, and it is employable in some specifications required.

Incidentally, although in this embodiment the pump cell voltage Vp is forced to vary and the decision on the presence or absence of a disconnection is made on the basis of the pump cell current variation $\Delta Ip$ at that time, it is also appropriate that the pump cell current Ip is forcibly varied and the decision on the presence or absence of a disconnection is made on the basis of the variation $\Delta Vp$ of the pump cell voltage Vp at that time. A description of this operation will be given with reference to FIG. 9. The pump cell current Ip is forced to vary in the step S402. This processing acts as the test signal inputting means. Subsequently, the step S403 is executed to input the pump cell voltage variation $\Delta Vp$ forming a response signal, which develops in response to the forced variation of the pump cell current Ip. In the next step S404, contrary to the case of the forced variation of the pump cell voltage Vp, a decision is made as to whether or not the pump cell voltage variation $\Delta Vp$ exceeds a prescribed value. Naturally, this prescribed value is different from that in the case of the pump cell voltage being formed to vary. The decision in the step S404 becomes affirmative when the pump cell 1 is in a disconnected condition. That is, if there is no disconnection, the pump cell voltage variation $\Delta Vp$ to be detected corresponds to a voltage drop in the pump cell 1a and the impedance for the alternating current component in the pump cell 1a is low as mentioned above so that the pump cell voltage variation $\Delta Vp$ is suppressible to a low value.

Figure 19:
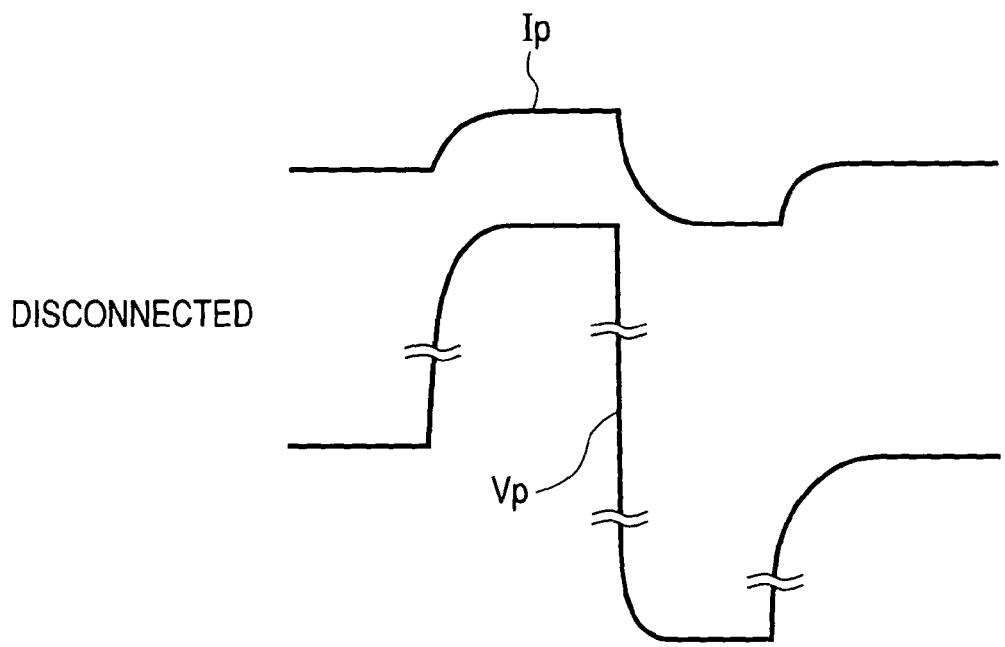
FIG. 19 is a second timing chart useful for explaining the contents of control for gas sensor abnormality detection according to a modification of the embodiment.

On the other hand, if there is a disconnection, the voltage drop increases by an amount corresponding to the impedance in the disconnected portion, so that pump cell voltage variation $\Delta Vp$ becomes large as shown in FIG. 19. Since the impedance of the pump cell 1a is low as mentioned above, the increasing degree of the pump cell voltage variation $\Delta Vp$ at the occurrence of a disconnection with respect to that at the non-occurrence of a disconnection becomes extremely large.

Thus, it is possible to accurately achieve the disconnection detection on the pump cell 1a without receiving the influence of the interference currents of the other cells 1b and 1c and others.

(Monitor Cell Disconnection Detection)

Figure 20:
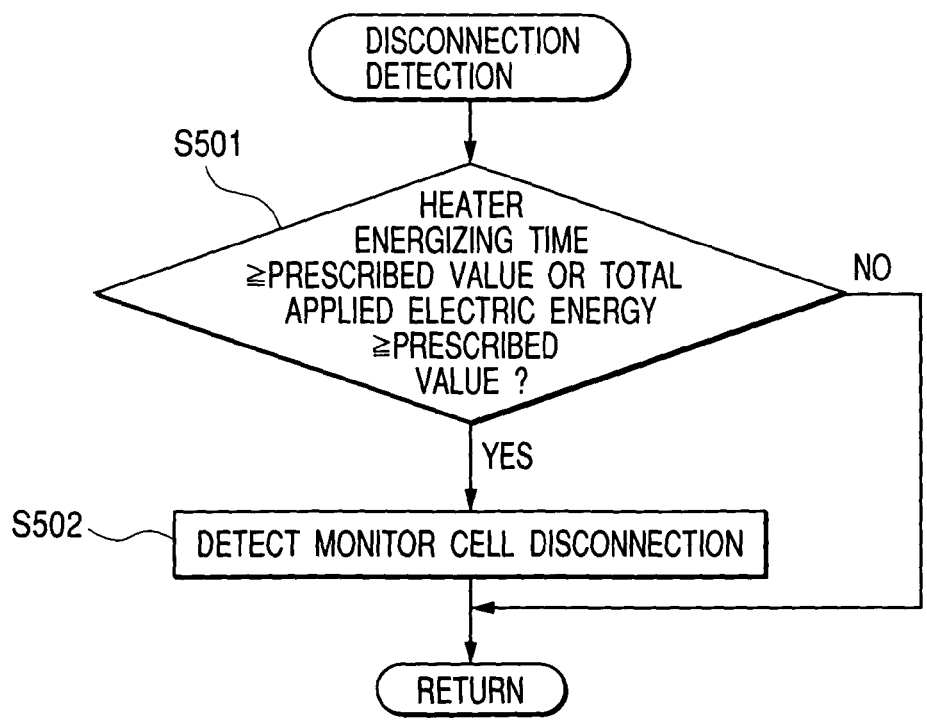
FIG. 20 is a third flow chart showing the contents of control for gas sensor abnormality detection to be implemented in the microcomputer constituting the gas concentration detecting apparatus.
Figure 21:
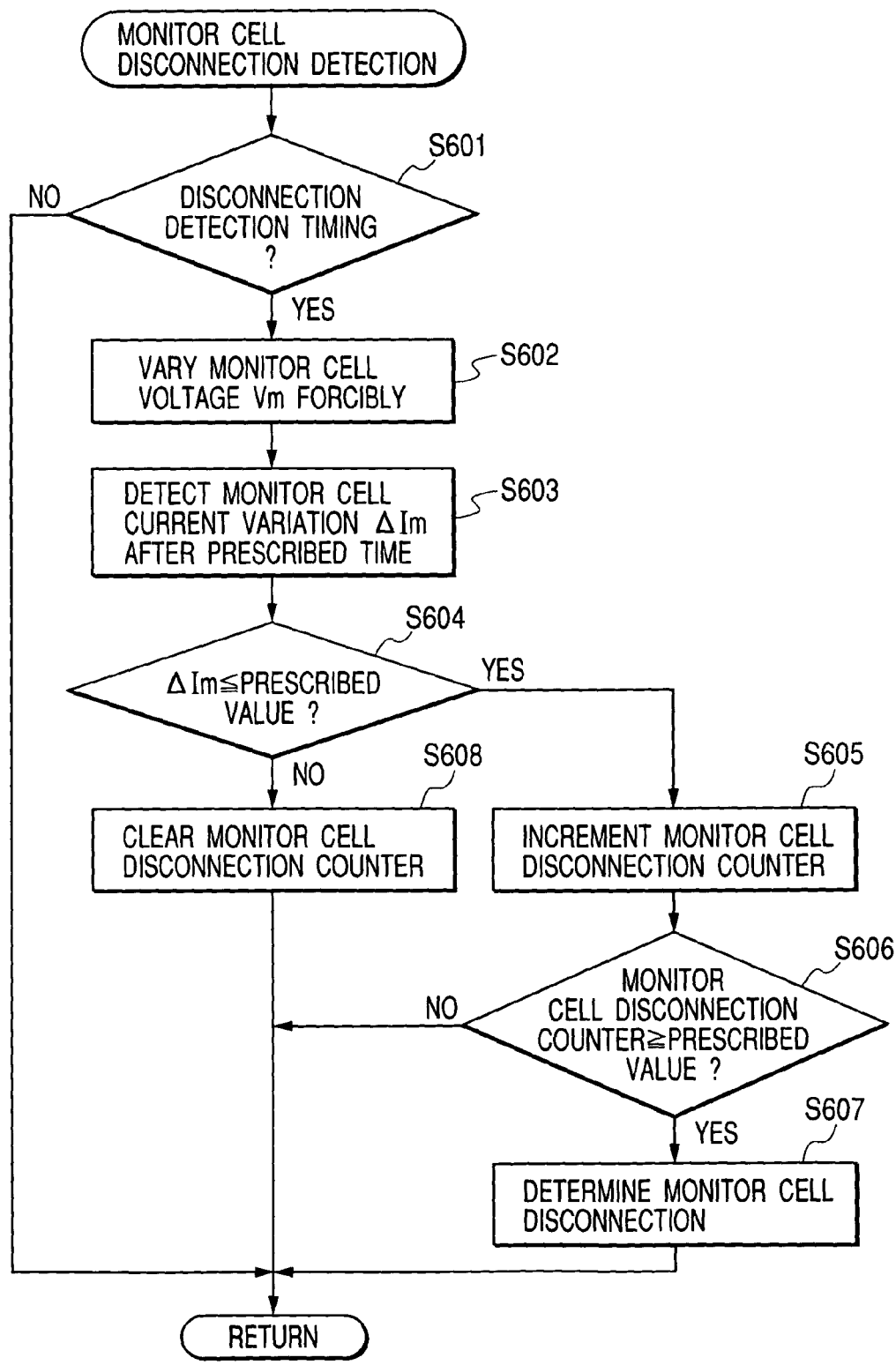
FIG. 21 is a fourth flow chart showing the contents of control for gas sensor abnormality detection to be implemented in the microcomputer constituting the gas concentration detecting apparatus.

FIGS. 20 and 21 are illustrations of disconnection detection processing on the monitor cell 1b. In a step S501, an energizing (current-supplying) time for the heater 13 (which will hereinafter be referred to equally as a "heater energizing time") is compared with a predetermined prescribed value to make a decision on whether or not it is equal to or more than the prescribed value. The heater energizing time is measured by a timer which functions as a temperature state detecting means and which counts the elapsed time from the start of energizing of the heater 13. If the decision indicates that the heater energizing time falls below the prescribed value, the operational flow returns. In the case of the affirmative decision, the operational flow advances to a step S502 to implement the monitor cell disconnection detection. The step S501 is processing acting as an inhibiting means.

The monitor cell disconnection detection processing (step S502) is conducted as in the case of the pump cell disconnection detection processing (step S302). First, in a step S601, a decision is made on the timing of the disconnection detection. In the case of the affirmative decision, the operational flow advances to a step S602. On the other hand, in the case of the negative decision, the operational flow returns. In the step S601, as with the pump cell disconnection processing, the affirmative decision is made every predetermined control cycle to implement the step S602 and subsequent processing.

The step S602 acts as a test signal inputting means to force the monitor cell voltage Vm to vary. At this time, the switch 245 is turned on in response to a control signal from the I/O 1 to make a connection of a resistor 244. An instruction voltage from the D/A 0 is slightly shifted to the positive side with respect to the voltage value immediately before and is then shifted slightly from this state to the negative side with the immediately-before voltage value. This produces a voltage variation, that is, the monitor cell voltage Vm is shifted to the positive and negative sides with respect to the immediately-before voltage value.

A step S603 is processing acting as a response signal detecting means to obtain a variation $\Delta Im$ of the monitor cell current Im flowing in response to the forced variation of the monitor cell voltage Vm. In this case, after the start of the voltage variation, the monitor cell current variation $\Delta Im$ is detected after the elapse of a predetermined prescribed time. The prescribed time will be mentioned later.

Steps S604 to S608 function as a decision means. First, in the step S604, the monitor cell current variation $\Delta Im$ detected is compared with a predetermined prescribed value to make a decision on whether or not it is below the prescribed value. In the case of the affirmative decision, the operational flow proceeds to the step S605 to increment the monitor cell disconnection counter by "1".

Figure 22:
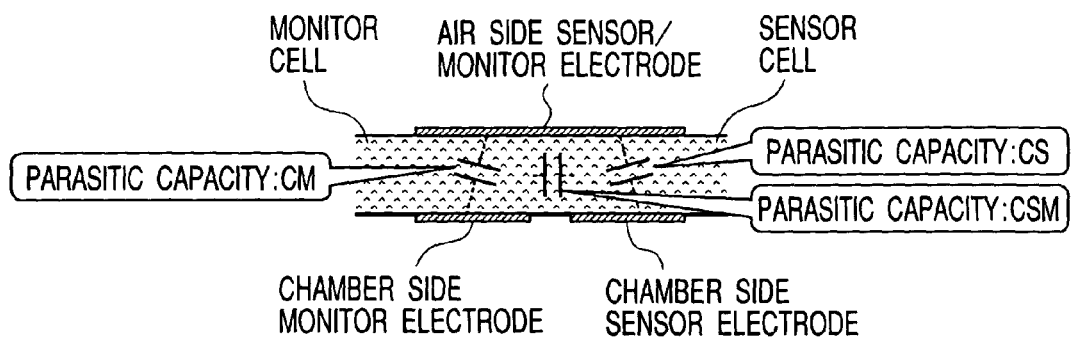
FIG. 22 shows a second cell for explaining the contents of control for gas sensor abnormality detection.
Figure 23:
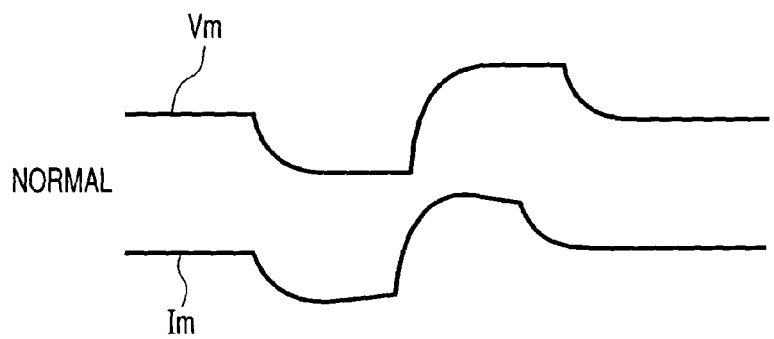
FIG. 23 is a sixth timing chart useful for explaining the contents of control for gas sensor abnormality detection.

In the step S604, the affirmative decision is made when the monitor cell 1b is in a disconnected condition. As in the case of the pump cell 1a, a parasitic capacity exists between the electrodes 123 and 125 of the monitor cell 1b. However, it is not simple unlike the pump cell 1a. That is, in the monitor cell 1b, the electrode 125 confronting the air duct 105 is made in common to the sensor cell 1c, and the other electrode 123 and the electrode 124 of the sensor cell 1c are placed to confront the same chamber 102 and located close to each other. Therefore, with respect to the monitor cell 1b and the sensor cell 1c, as illustratively shown in FIG. 22, in addition to a parasitic capacity CM between the electrodes 123 and 125 of the monitor cell 1b, there exist a parasitic capacity CS between the electrodes 124 and 125 of the sensor cell 1c and a parasitic capacity (which will hereinafter be refereed to equally as a "sensor-monitor parasitic capacity) CSM between the chamber side monitor electrode 123 and the chamber side sensor electrode 124. Accordingly, through the forced variation of the monitor cell voltage Vm, a monitor cell current variation $\Delta Im$ develops according to the parasitic capacities CM, CS and the sensor-monitor parasitic capacity CSM as shown in FIG. 23 if no disconnection occurs in the monitor cell 1b. In this case, the sensor parasitic capacity CS and the sensor-monitor parasitic capacity CSM increase the monitor parasitic capacity CM and, hence, the monitor cell current variation $\Delta Im$ becomes larger accordingly.

Figure 24:
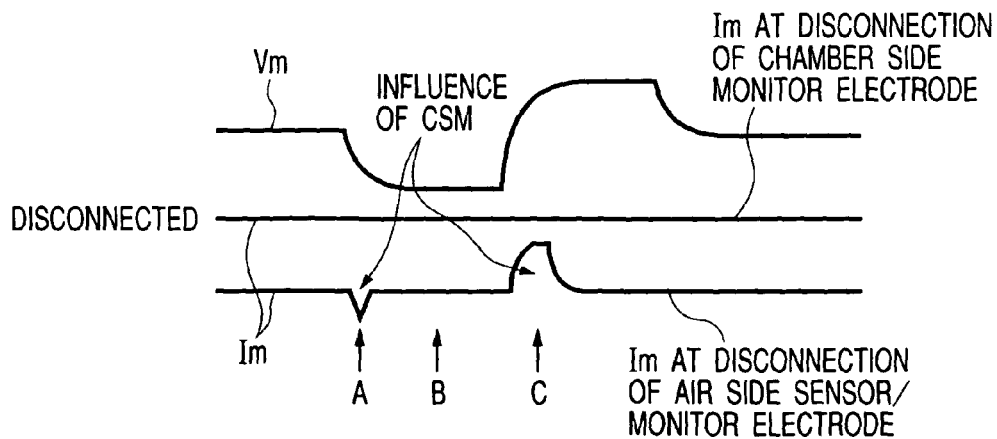
FIG. 24 is a seventh timing chart useful for explaining the contents of control for gas sensor abnormality detection.

On the other hand, assuming that a disconnection occurs in the monitor cell 1b, in a case in which a signal line on the chamber side monitor electrode 123 side is in a disconnected condition and in a case in which a signal line on the air side sensor/monitor electrode 125 side is in a disconnected condition, behaviors occur as shown in FIG. 24. That is, for the monitor cell voltage Vm, an instruction voltage from the D/A 0 is varied, and it is transmitted through the LPF 241, the operational amplifier 242, the resistor 243 and the resistor 244 to the chamber side monitor electrode 123, and if a signal line on the chamber side monitor electrode 123 side is in a disconnected condition, the monitor cell current variation ΔIm does not occur irrespective of the variation of the D/A 0 instruction voltage. In this case, the aforesaid prescribed value can be set to an upper limit value at which the monitor cell current variation ΔIm can be considered to be at zero.

On the other hand, in a case in which a disconnection occurs at a signal line on the air aide sensor/monitor electrode 125 side, the chamber side monitor electrode 123 and the chamber side sensor electrode 124 are capacity-coupled to each other, thus generating a monitor cell current variation ΔIm. In this case, since the sensor-monitor parasitic capacity CSM is smaller as compared with the monitor cell parasitic capacity CM or the like, the generated monitor cell current variation ΔIm is smaller than the monitor cell current variation ΔIm to be detected in a state where no disconnection occurs, and the current variation time becomes short.

Therefore, the prescribed value for the monitor cell current variation ΔIm varies according to the setting of the aforesaid prescribed time. That is, if the monitor cell current variation ΔIm is obtained at a point A or C in FIG. 24, the monitor cell current variation ΔIm is affected by the sensor-monitor parasitic capacity CSM and, hence, there is a need to set the proscribed value to a value larger than the above-mentioned upper limit value. Moreover, the monitor cell current variation ΔIm is obtained at a point B where the sensor-monitor parasitic capacity CSM does not exert influence on the monitor cell current variation ΔIm, as with the disconnection related to the chamber side monitor electrode 123, the prescribed value becomes an upper limit value which can be considered to be zero.

Incidentally, in a present exemplary embodiment, since the disconnection detection is made on the basis of the current variation ΔIm responsive to the forced variation of the monitor cell voltage Vm, as in the case of the disconnection detection in the pump cell 1a, it is possible to more accurately make a decision on the presence or absence of a disconnection in the monitor cell 1b, as compared to the technique of merely checking the presence of absence of a current.

Referring again to FIG. 21, when the monitor cell current variation ΔIm is below the prescribed value and the monitor cell disconnection counter is incremented (steps S604 and S605), the step S606 follows to compare the count value of the monitor cell disconnection counter with a predetermined prescribed value to make a decision as to whether or not it reaches the prescribed value. In the case of the negative decision, the operational flow returns. On the other hand, in the case of the affirmative decision, the operational flow advances to the step S607 to determine that the monitor cell 1b is in a disconnected condition. These series of processing are substantially the same as the steps S405 to S407 in the pump cell 1a disconnection detection processing, and a decision on a disconnection in the monitor cell 1b can be made with high accuracy.

On the other hand, if the monitor cell current variation ΔIm falls below the prescribed value and the decision in the step S604 is negative, the operational flow returns after the monitor disconnection counter is cleared in the step S608. Therefore, as in the case of the step S408 on the disconnection detection processing on the pump cell 1a, even if the monitor cell current variation ΔIm falls suddenly below the prescribed value, it is possible to avoid that a decision on disconnection in the monitor cell 1b is made in error.

Figure 25:
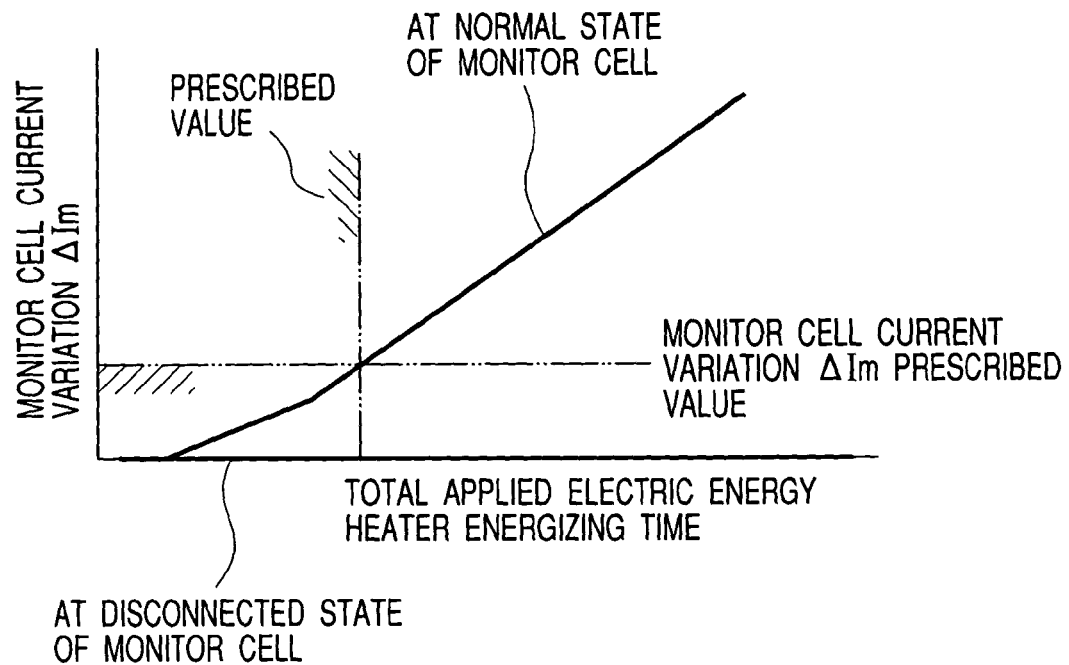
FIG. 25 is a second graphic illustration useful for explaining the contents of control for gas sensor abnormality detection.

Moreover, the monitor cell disconnection detection processing (step S502) is conducted only when the heater energizing time exceeds a prescribed value. That is, as shown in FIG. 25, the temperatures of the solid electrolyte layers 111 and 112 rises with the heater energizing time so that the impedance becomes lower and the aforesaid parasitic capacities CM, CS and CSM become larger, while the parasitic capacities CM, CS and CSM are small for a short heater energizing time and difficulty is experienced in obtaining a sufficiently large current variation ΔIm in response to the forced variation of the monitor cell voltage Vm so that it is difficult to make a clear discrimination from the occurrence of a disconnection. Moreover, the S/N can be insufficient. Therefore, the monitor cell disconnection detection processing (step S502) is conducted only when the heater energizing time exceeds the prescribed value, thus enhancing the decision accuracy on the disconnection in the monitor cell 1b.

In this connection, although in this embodiment the decision on whether the monitor cell disconnection detection processing (step S502) is conducted or not is made on the basis of the heater energizing time, for more accuracy, it is appropriate that the decision is made on the basis of the total applied electric energy used for the heater 13. In this case, for example, an electric power is detected every disconnection detection timing (S601) and the detected electric power is accumulated and the accumulated value thereof is used as the applied electric energy. Alternatively, it is also appropriate that the voltage of the battery 26 serving as a power supply for the heater 13 is detected at the power-on so that a decision on whether or not the temperatures of the solid electrolyte layers 111 and 112 rise sufficiently, that is, a decision on the timing of the implementation of the monitor cell disconnection detection processing (step S502), is made on the basis of a value obtained by multiplying the detected voltage by the aforesaid heater energizing time. As an implementation condition on the monitor cell disconnection detection processing (step S502), other parameters are also acceptable provided that they increase monotonously in accordance with the applied electric energy.

Furthermore, with respect to the cells other than the monitor cell 1b undergoing the disconnection detection, as an embodiment, the present exemplary embodiment includes that the impedance detection processing is conducted in the steps S201 to S203 to detect the temperature states of the solid electrolyte layers 111 and 112. However, for example, in the case of the impedance detection being made with respect to the sensor cell 1c, a circuit for changing the sensor cell voltage becomes necessary like the monitor cell 1b or the like, which complicates the configuration and increases the control burden. Therefore, the above-described embodiment is more practical.

Incidentally, although in this embodiment the decision is limited to only the presence or absence of disconnection in the monitor cell 1b, it is also possible to make a decision as to which of the electrodes 123 and 125 of the monitor cell 1b is in a signal line disconnected condition. That is, when the monitor cell current variation ΔIm is sampled at the point A or C in FIG. 24, the monitor cell current variation ΔIm in the disconnected condition differs in magnitude between the disconnection related to the chamber side monitor electrode 123 and the disconnection related to the air side sensor/monitor electrode 125. Therefore, when two types of prescribed values different in magnitude from each other are set, and if the monitor cell current variation ΔIm falls below the smaller prescribed value, a decision is made that the disconnection of the chamber side monitor electrode 123 occurs. On the other hand, if the monitor cell current variation ΔIm is more than the smaller prescribed value but being below the larger prescribed value, a decision is made that the air side sensor/monitor electrode 125 is placed into a disconnected condition.

In this connection, in FIG. 24, the monitor cell current variation ΔIm shows different values at the points A and C. This is because the range of the voltage variation ΔVm of the monitor cell voltage Vm is larger at the latter point C.

In addition, without making a decision as to the presence or absence of a disconnection on the basis of the monitor cell current variation ΔIm, it is also appropriate that a decision on the presence or absence of a disconnection is made on the basis of an impedance by dividing the monitor cell voltage variation ΔVm by the monitor cell current variation ΔIm. In a case in which the impedance exceeds a prescribed value, a decision is made as the occurrence of a disconnection. In this case, the impedance detection processing (step S104) is conducted for the impedance. Naturally, the decision can also be made on the basis of an admittance.

Figure 26:
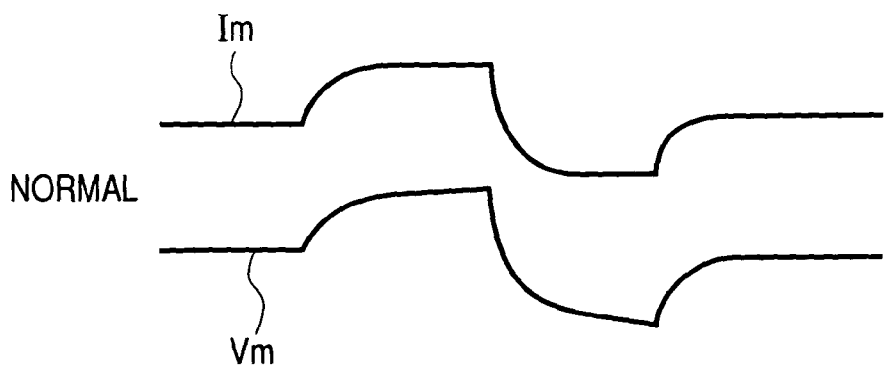
FIG. 26 is a first timing chart useful for explaining the contents of control for gas sensor abnormality detection according to another modification of the embodiment.

Still additionally, as mentioned in the "pump cell disconnection detection", it is also appropriate to detect a variation of the voltage by forcibly varying the current to be applied to a cell. That is, the monitor cell current Im is forcibly varied, and a decision on the presence or absence of a disconnection is made on the basis of the monitor cell voltage variation ΔVm at that time. Explaining with reference to FIG. 21, the monitor cell current Im is forcibly varied in the step S602. This processing acts as a test signal inputting means. Subsequently, in the step S603, a monitor cell voltage variation ΔVm forming a response signal is inputted (detected) which develops in response to the forced variation of the monitor cell current Im, then followed by the step S604 to make a decision as to whether or not the monitor cell voltage variation ΔVm exceeds a prescribed value, unlike the case of the forced variation of the monitor cell voltage Vm. The decision in the step S604 is made affirmative when the monitor cell 1b is in a disconnected condition. That is, if there is no disconnection, the monitor cell voltage variation ΔVm to be detected corresponds to only a voltage drop in the monitor cell 1b and the impedance for the alternating current component in the monitor cell 1b is low as mentioned above and, hence, the monitor cell voltage variation ΔVm is suppressed to a low value as shown in FIG. 26.

Figure 27:
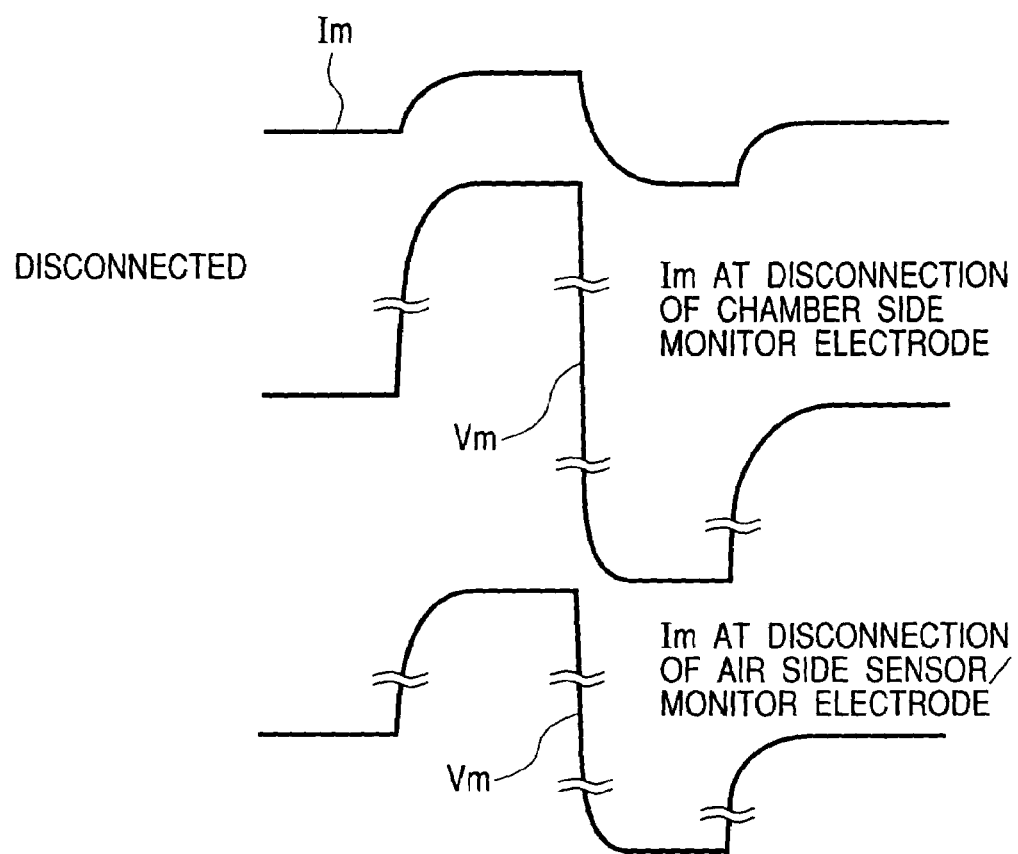
FIG. 27 is a second timing chart useful for explaining the contents of control for gas sensor abnormality detection according to another modification of the embodiment.

On the other hand, in the case of the occurrence of a disconnection, the voltage drop increases by an amount corresponding to the impedance in the disconnected portion and, hence, the monitor cell voltage variation ΔVm increases as shown in FIG. 27. Since the impedance in the monitor cell 1b is extremely low as mentioned above, the increasing degree of the monitor cell voltage variation ΔVm at the occurrence of a disconnection with respect to that at the non-occurrence of a disconnection becomes extremely large. Incidentally, the monitor cell voltage variation ΔVm varies due to the influence of the parasitic capacity CSM between the occurrence of a disconnection of the chamber side monitor electrode 123 and the occurrence of a disconnection of the air side sensor/monitor electrode 125.

Thus, the detection of the disconnection in the monitor cell 1b can be made with high accuracy without receiving the influence of the interference currents of the other cells 1a and 1c, or the like.

(Sensor Cell Disconnection Detection)

Figure 28:
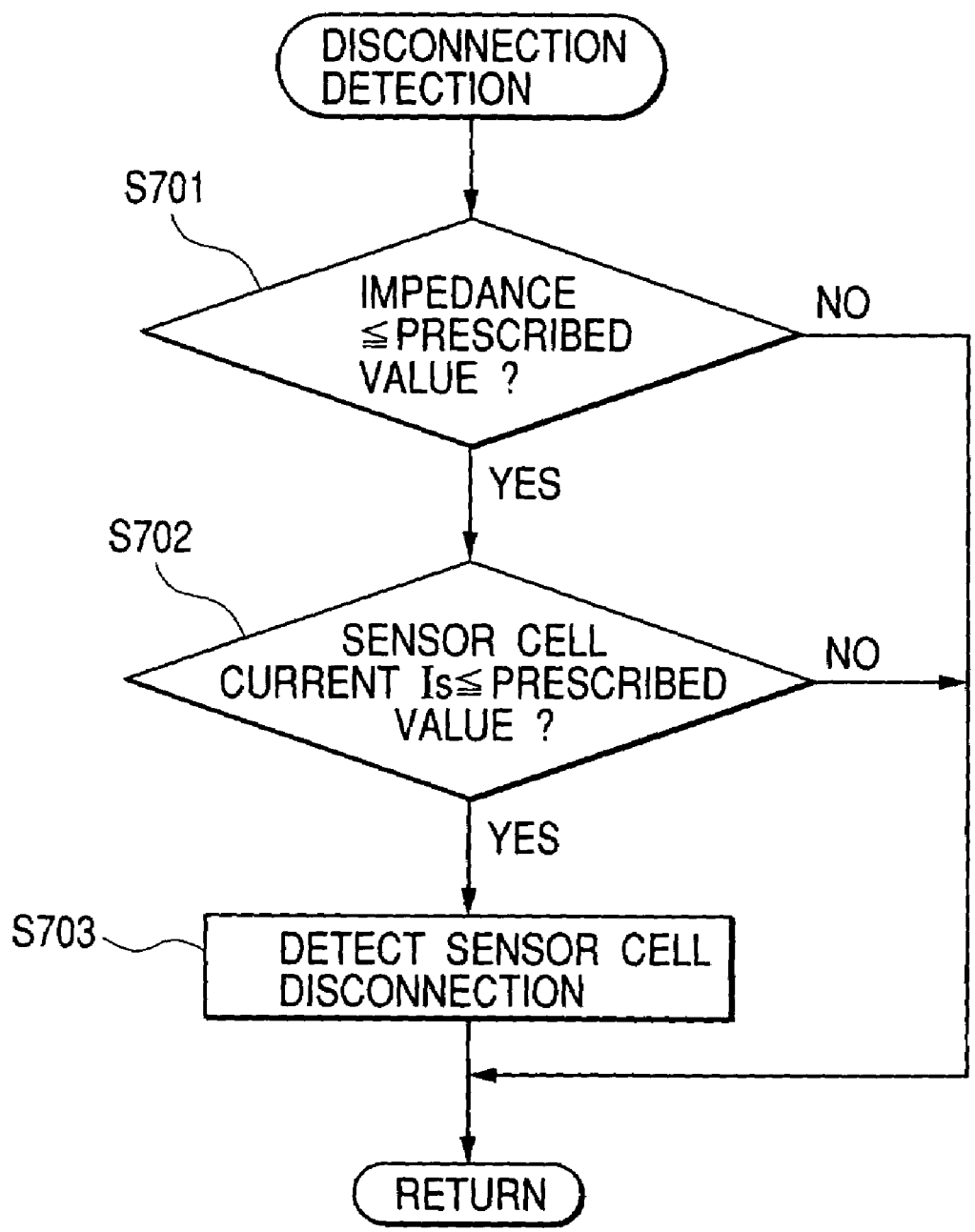
FIG. 28 is a fifth flow chart showing the contents of control for gas sensor abnormality detection to be implemented in the microcomputer constituting the gas concentration detecting apparatus.
Figure 29:
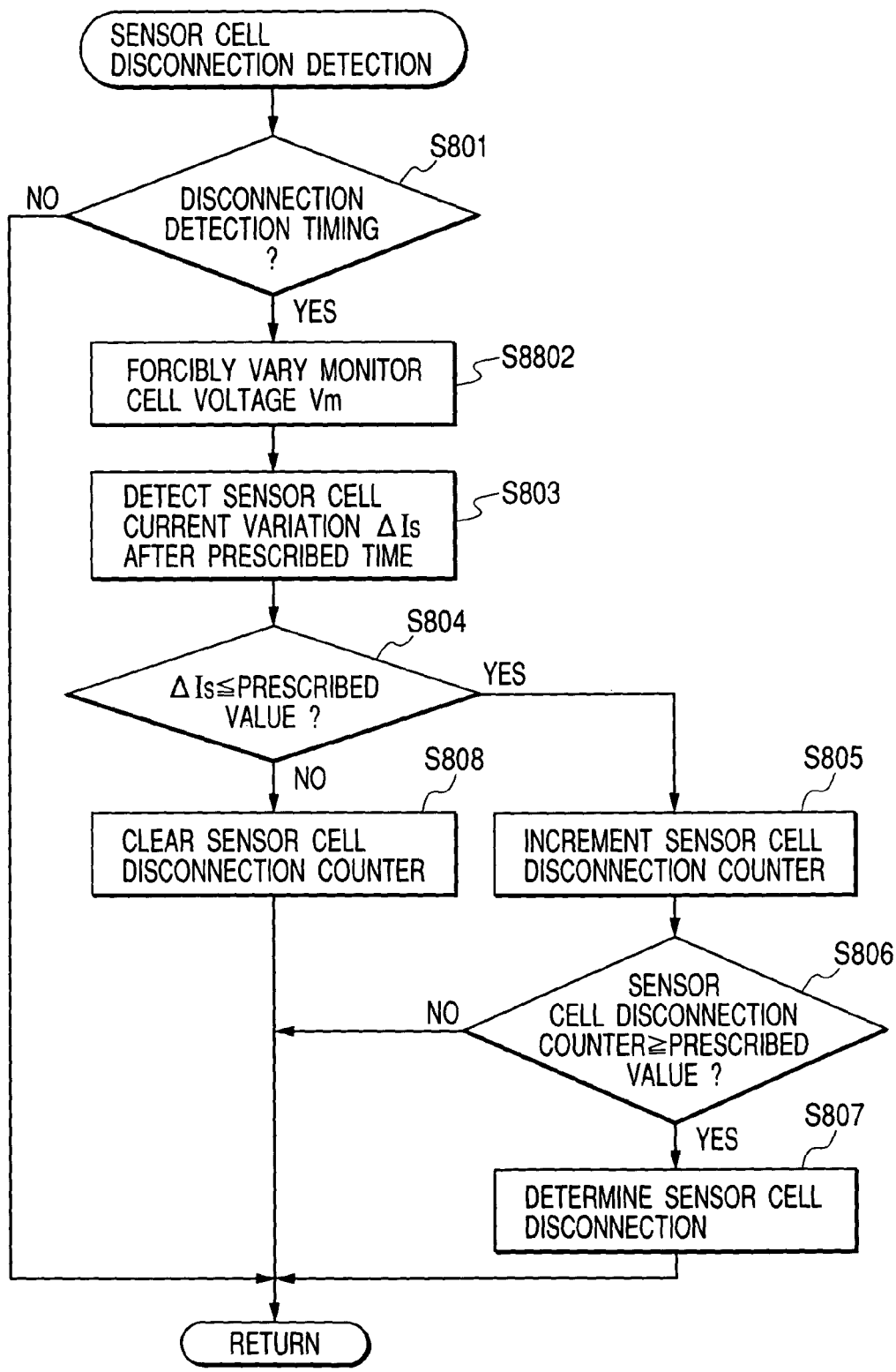
FIG. 29 is a sixth flow chart showing the contents of control for gas sensor abnormality detection to be implemented in the microcomputer constituting the gas concentration detecting apparatus.

FIGS. 28 and 29 are illustrations of the disconnection detection processing for the sensor cell 1c. In a step S701, as in the case of the pump cell disconnection detection (step S301), an impedance ZAC detected in the impedance detection processing (step S104) is compared with a predetermined prescribed value. If it exceeds the prescribed value, the operational flow returns. On the other hand, if it falls below the prescribed value, the operational flow advances to a step S702. In the step S702, a decision is made as to whether or not a sensor cell current Is is below a prescribed value. In the case of the negative decision, the operational flow returns. On the other hand, in the case of the affirmative decision, a step S703 is implemented to carry out the sensor cell disconnection detection processing. Incidentally, if the sensor cell current Is is extremely large, the current variation (see FIG. 30) at the implementation of the disconnection detection which will be mentioned later goes out of the A/D input dynamic range. Therefore, the step S702 is designed so as to inhibit the disconnection detection in such a situation.

In the sensor cell disconnection detection processing (step S703), first, in a step S801, a decision is made on the disconnection detection timing. In the case of the affirmative decision, the operational flow proceeds to a step S802. On the other hand, in the case of the negative decision, the operational flow returns. As in the case of the pump cell disconnection detection processing, in the step S801, the affirmative decision is made every predetermined control cycle of the microcomputer 28 to implement the step S802 and subsequent processing.

The step S802 functions as a test signal inputting means to forcibly vary the monitor cell voltage Vm. As with the monitor cell disconnection detection processing (step S602), this is carried out by varying an instruction voltage from the D/A 0.

The step S803 functions as a response signal detecting means to, after the start of the forced variation of the monitor cell voltage Vm, detect a sensor cell current variation ΔIs at the elapse of a predetermined prescribed time. The prescribed time will be described later.

Steps S804 to S808 serve as a decision means. First, in the step S804, the sensor cell current variation ΔIs detected is compared with a predetermined prescribed value to make a decision on whether or not it is below the prescribed value. In the case of the affirmative decision, the operational flow proceeds to the step S805 to increment the sensor cell disconnection counter by "1".

Figure 30:
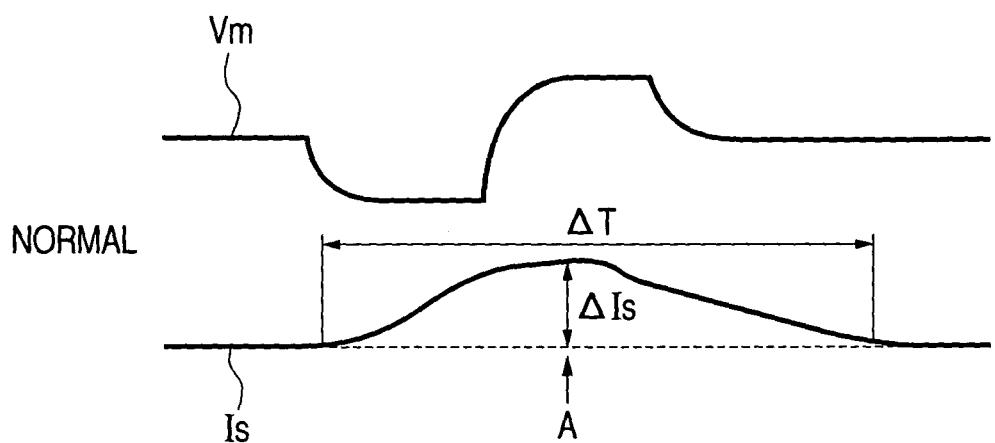
FIG. 30 is an eighth timing chart useful for explaining the contents of control for gas sensor abnormality detection.

In the step S804, the affirmative decision is made when a signal line for the chamber side sensor electrode 124 in the sensor cell 1c is in a disconnected condition. In the sensor cell 1c and the monitor cell 1b, since the electrodes 123 and 124 are provided to confront the same chamber 102, the oxygen pumping ability from/into the chamber 102 varies due to the forced variation of the monitor cell voltage Vm, which affects the sensor cell 1c. That is, when the oxygen concentration varies in the chamber 102, if there is no disconnection in the sensor cell 1c, as shown in FIG. 30, a current variation ΔIs occurs with respect to the sensor cell current Is immediately before.

Figure 31:
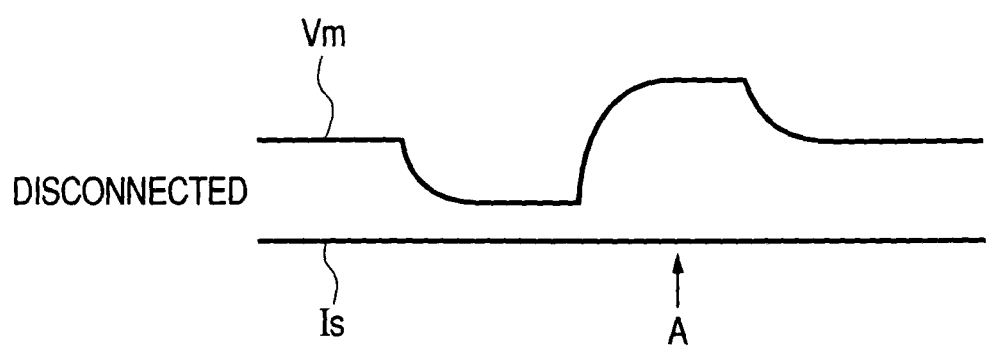
FIG. 31 is a ninth timing chart useful for explaining the contents of control for gas sensor abnormality detection.

On the other hand, if a disconnection occurs in the sensor cell 1c, no sensor cell current variation ΔIs occurs as shown in FIG. 31. In this case, since the electrode 125 of the sensor cell 1c confronting the air duck 105 is made in common to the monitor cell 1b, if the decision is made as to no occurrence of disconnection with respect to the electrode 125, then this signifies that the disconnection occurs in the chamber side sensor electrode 124.

When the sensor cell current variation ΔIs is below the prescribed value and the sensor cell disconnection counter is incremented (steps S804 and S805), in the step S806, the count value of the sensor cell disconnection counter is compared with a predetermined prescribed value to make a decision as to whether or not it reaches the prescribed value. In the case of the negative decision, the operational flow returns. On the other hand, in the case of the affirmative decision, the operational flow proceeds to the step S807 to determined that the sensor cell 1c is in a disconnected condition. These series of processing are substantially the same as those of the steps S405 to S407 in the disconnection detection processing for the pump cell 1a, and the decision on the disconnection of the sensor cell 1c can be made with high accuracy.

In this connection, if the decision in the step S804 is negative, that is, when the sensor cell current variation ΔIs exceeds the prescribed value, the operational flow returns after the sensor cell disconnection counter is cleared in the step S808. Therefore, as in the case of the step S408 on the disconnection detection processing on the pump cell 1a, even if the sensor cell current variation ΔIs falls suddenly below the prescribed value, it is possible to avoid that a decision on disconnection in the monitor cell 1b is made in error.

Moreover, since the condition of the sensor cell disconnection detection processing (step S703) is that the impedance falls below the prescribed value, as in the case of the pump cell disconnection detection processing (step S301), the sensor cell disconnection detection processing is conducted only when the impedance is low and a sufficiently large sensor cell current variation ΔIs is obtained, thus enhancing the accuracy of the decision on the disconnection in the sensor cell 1c.

The disconnection of the sensor cell 1c is detected in this way. There is no need to forcibly vary the sensor cell voltage Vs. Moreover, since, as in the case of the step S802, the monitor cell voltage Vm is forcibly varied in the disconnection detection of the monitor cell 1b (step S502) or the impedance detection processing (step S104) (steps S602, S201), the test signal inputting means also works for these processing, which simplifies the configuration.

Incidentally, if the time of the forced variation of the monitor cell voltage is too long, the oxygen concentration in the chamber 102 varies largely and a larger sensor cell current variation ΔIs develops accordingly. However, the time ΔT needed until the oxygen concentration returns to its original value becomes long and the time for which difficulty is encountered in normally performing the detection of NOx concentration is prolonged accordingly. Therefore, it is preferable that the length of the time of the forced variation of the monitor cell voltage is set to be as short as possible within a range where a sensor cell current variation ΔIs is obtainable so that the decision on the presence or absence of disconnection can be made with accuracy.

Conversely, even if the time of the voltage variation ΔVm of the monitor cell voltage Vm is short, a current variation ΔIs of the sensor cell current Is occurs due to the parasitic capacity CSM between the monitor cell 1b and the sensor cell 1c as shown in FIG. 30. Therefore, it is also possible to make the disconnection detection utilizing this fact.

Still moreover, although, for the monitor cell disconnection detection, the current to be applied to the cell is forcibly changed to observe the voltage variation, it is also possible to make the sensor cell disconnection detection utilizing the forced variation of the monitor cell current Im. In FIG. 29, the monitor cell current Im is forcibly varied in the step S802, which serves as a test signal inputting means. The step S803 and subsequent processing are the same. That is, because of the forced variation of the monitor cell current Im, the oxygen concentration varies in the interior of the chamber 102 and the sensor cell current Is varies. Therefore, a binary decision is made on this magnitude.

Figure 32:
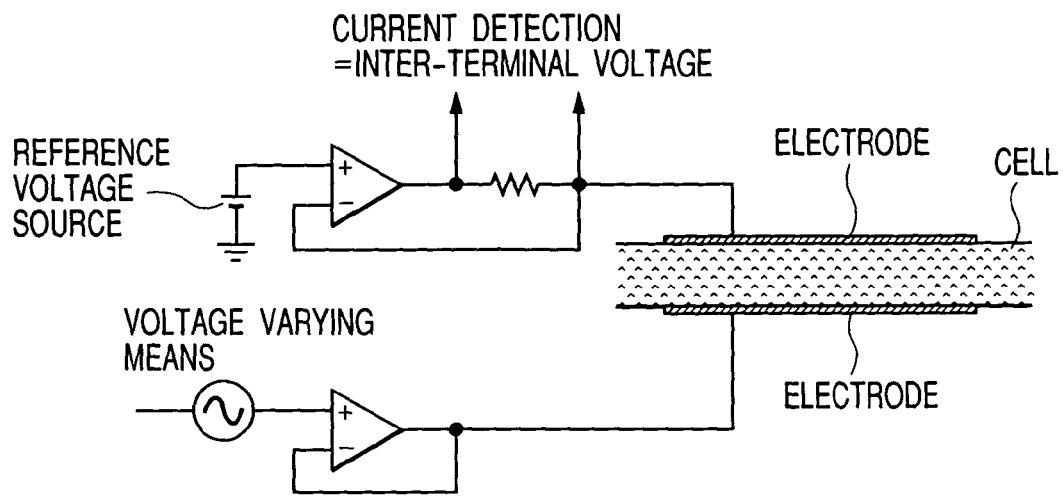
FIG. 32 is an illustration of a configuration of an essential part of a modification of the gas concentration detecting apparatus.

In addition, although in this embodiment the current detection and voltage variation of each of the pump cell 1a and the monitor cell 1b are made on the same electrode 121, 123 side, it is also appropriate that, as shown in FIG. 32, a reference voltage source is connected to a current detection side operational amplifier while a voltage varying means is connected to another operational amplifier.

Figure 33:
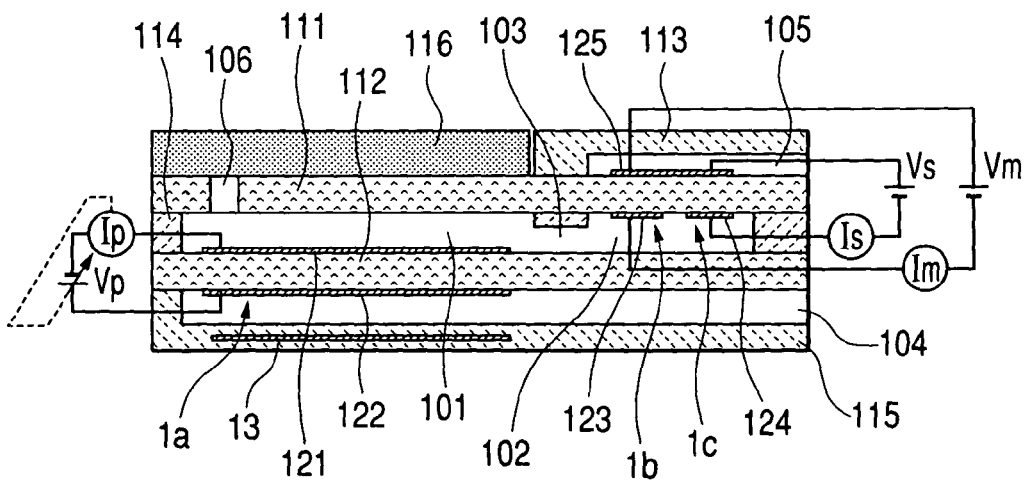
FIG. 33 is a cross-sectional view showing the gas sensor shown in FIG. 1, and is an illustration for explaining a control method for the gas sensor.
Figure 34:
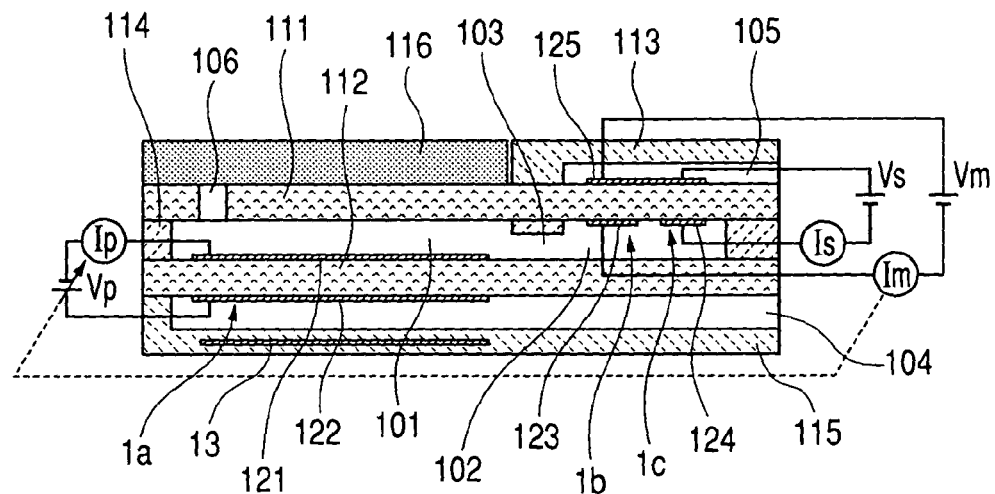
FIG. 34 is a cross-sectional view showing the gas sensor shown in FIG. 1, and is an illustration for explaining a modification of a control method for the gas sensor.

Still additionally, although this embodiment employs a control method shown in FIG. 33 in which a pump cell voltage Vp is set in accordance with an applied voltage map on the basis of a pump cell current Ip, the present exemplary embodiment is also applicable to a technique in which, as shown in FIG. 34, a pump cell voltage Vp is feedback-controlled on the basis of a monitor cell current Im so that the monitor cell current Im takes a predetermined value.

Figure 35:
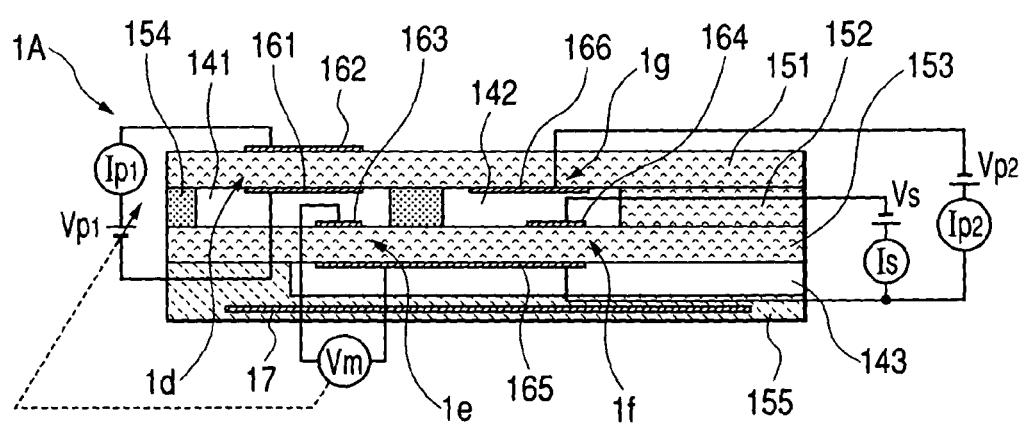
FIG. 35 is a cross-sectional view showing a modification of the gas sensor, and is an illustration for explaining a control method for the gas sensor.

Yet additionally, the gas sensor is not limited to the construction illustrated. FIG. 35 shows another example of a gas sensor to which the present exemplary embodiment is also applicable. This gas sensor, generally designated at reference numeral 1A, has a stacked construction in which built up in a thickness direction are solid electrolyte layers 151, 152, 153 made of a solid electrolyte material such as zirconia, a rate-determining layer 154 made of an insulating material such as porous alumina, a layer 155 made of an insulating material such as alumina or made of zirconia or the like, and others. It has an elongated configuration as a whole.

The solid electrolyte layer 152 and the rate-determining layer 154 are constructed as the same layer and interposed between the solid electrolyte layer 151 and the solid electrolyte layer 153. The rate-determining layer 154 is positioned at the tip side of the gas sensor 1A while the solid electrolyte layer 152 is positioned at the proximal side thereof. The solid electrolyte layer 152 and the rate-determining layer 154 are partially punched in a thickness direction, and two chambers 141 and 142 disposed in a longitudinal direction of the gas sensor 1A are formed between the solid electrolyte layers 151 and 152. The rate-determining layer 154 is located on the tip side of the gas sensor 1A for introducing a measured gas in the exterior of the gas sensor 1A into the first chamber 141 and for making a communication between the first chamber 141 and the second chamber 142 at the boundary portion between both the chambers 141 and 142.

An air duct 143, using the solid electrolyte layer 153 as a portion of a duct wall, is formed on the opposite side to the chambers 141 and 142 in a state where the solid electrolyte layer 153 is interposed therebetween. The tip side of the air duct 143 extends up to a position confronting the first chamber 141 so that the solid electrolyte layer 153 is interposed therebetween, and the air duct 143 is open to the atmosphere at the proximal portion of the gas sensor 1A. In a case in which the gas sensor 1A is used for an internal combustion engine, the gas sensor 1A, together with a holder member for holding the gas sensor 1A and others, is placed to penetrate a pipe wall of an exhaust pipe and the air duct 143 communicates with the exterior of the exhaust pipe.

At the position of the first chamber 141, a pair of electrodes 161 and 162 are provided on upper and lower surfaces of the solid electrolyte layer 151 to be in opposed relation to each other in a state where the solid electrolyte layer 151 is interposed therebetween, and the solid electrolyte layer 151 and the electrodes 161, 162 constitute a pump cell 1*d*. Of the electrodes 161 and 162 constituting the pump cell 1*d*, the electrode 161 confronting the chamber 141 is made of a noble metal such as Au—Pt inactive for the decomposition (reduction) of NOx.

Moreover, at the positions of the first chamber 141 and the air duct 143, a pair of electrodes 163 and 165 are provided on upper and lower surfaces of the solid electrolyte layer 153 to confront each other in a state where the solid electrolyte layer 153 is interposed therebetween, and the solid electrolyte layer 153 and the electrodes 163, 165 constitute a monitor cell 1*e*. Of the electrodes 163 and 165 constituting the monitor cell 1*e*, the electrode 163 confronting the chamber 141 is made of a noble meter such as Au—Pt inactive for the decomposition (reduction) of NOx. The electrode 165 confronting the air duct 143 extends up to a position of the second chamber 142 and is longer than the electrode 163. This electrode 165 acts as an electrode common to a sensor cell If and another pump cell 1*g*, which will be mentioned later.

At the position of the second chamber 142, a pair of electrodes 164 and 165 are provided on upper and lower surfaces of the solid electrolyte layer 153 to confront each other in a state where the solid electrolyte layer 153 is interposed therebetween. The solid electrolyte layer 153 and the electrodes 164, 165 organize the sensor cell 1*f*.

Still moreover, an electrode 166 is formed on the solid electrolyte layer 151 to confront the second chamber 142, and the solid electrolyte layers 151 to 153 and the electrodes 166 and 165 constitute another pump cell 1*g*. As with the sensor cell 1*f*, in this another pump cell 1*g*, one electrode 166 confronts the second chamber 142 while the other electrode 165 confronts the air duct 143.

Of the electrodes 164 and 166 confronting the second chamber 142, the electrode 164 of the sensor cell If is made of a noble metal such as Pt active for the decomposition (reduction) of NOx, and the electrode 166 of the another pump cell 1*g* is made of a noble metal such as Au—Pt inactive for the decomposition (reduction) of NOx.

Yet moreover, a line pattern such as Pt is buried in a layer 155, together with the solid electrolyte layer 153, constituting a duct wall of the air duct 143, thereby producing a heater 17 for heating the entire gas sensor 1A. The heater 17 is of an electrical type which generates joule heat when energized.

In this gas sensor 1A, an applied voltage to the pump cell 1*d* is feedback-controlled on the basis of an electromotive voltage developing in the monitor cell 1*e* so that the electromotive voltage becomes a reference voltage, that is, the oxygen concentration in the interior of the first chamber 141 becomes constant and takes a low value, and the oxygen in the interior of the first chamber 141 is discharged. The oxygen in the interior of the second chamber 142 communicating with the first chamber 141 is also discharged by an amount nearly equal thereto.

In addition, the oxygen remaining in the interior of the second chamber 142 is ejected by the other pump cell 1*g*. In the sensor cell 1*f*, a current flows due to the decomposition of NOx at the electrode 164 confronting the second chamber 142. This current corresponds to the concentration of NOx in the second chamber 142.

Also in the gas sensor 1A thus constructed, the cell disconnection can be detected without receiving the influence of the other cells or the like in a manner such that a voltage variation is given between the cell electrodes to produce a current variation depending on a parasitic capacity between the electrodes.

Figure 36:
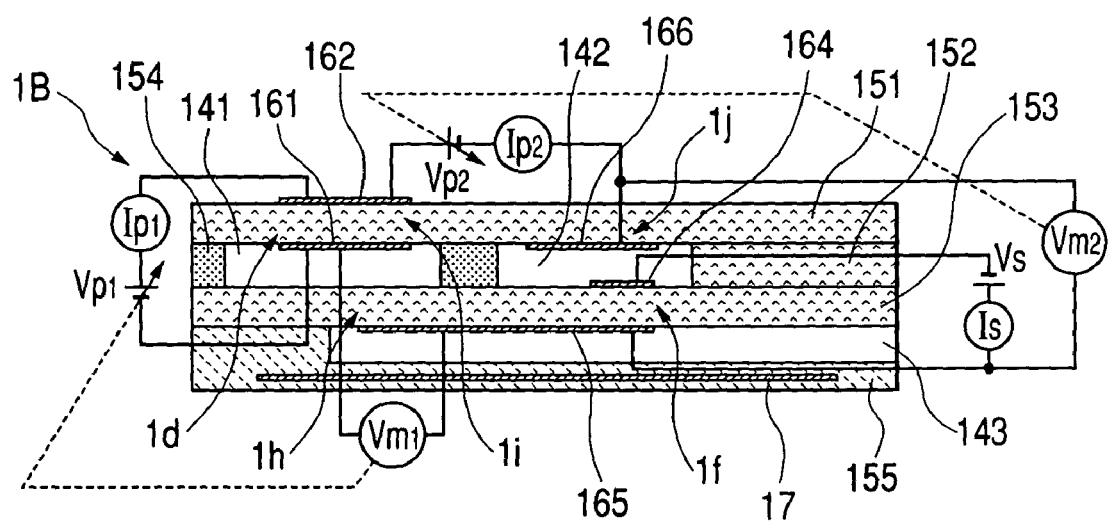
FIG. 36 a cross-sectional view showing another modification of the gas sensor, and is an illustration for explaining a control method for the gas sensor.

Alternatively, the present exemplary embodiment is also applicable to a gas sensor generally designated at reference numeral 1B in FIG. 36. The gas sensor 1B has the same construction as that shown in FIG. 35 except electrode configuration. In this electrode configuration, the electrode 163 shown in FIG. 35 is omitted. The solid electrolyte 151 and the electrodes 161 and 162 between which the solid electrolyte layer 151 is sandwiched constitute a first pump cell 1*d*, and the solid electrolyte layers 151 to 153 and the electrodes 161 and 165 constitute a first monitor cell 1*h*. An applied voltage to between the electrodes 161 and 162 of the first pump cell 1*d* is feedback-controlled on the basis of an electromotive voltage developing in the first monitor cell 1*h* so that the electromotive voltage becomes a reference voltage, that is, the oxygen concentration in the interior of the first chamber 141 becomes constant and takes a low value, and the oxygen in the interior of the first chamber 141 is discharged.

In addition, the solid electrolyte layer 151 and the electrodes 166 and 162 between which the solid electrolyte layer 151 is interposed constitute a second pump cell 1*i*, and the solid electrolyte layers 151 to 153 and the electrodes 166 and 165 organize a second monitor cell 1*j*. An applied voltage to between the electrodes 166 and 162 of the second pump cell 1*i* is feedback-controlled on the basis of an electromotive voltage developing in the second monitor cell 1*j* so that the electromotive voltage becomes a reference voltage, that is, the oxygen concentration in the interior of the first chamber 142 becomes constant and takes a low value, and the oxygen in the interior of the second chamber 142 is discharged.

The solid electrolyte layer 153 and the electrodes 164 and 165 between which the solid electrolyte layer 153 is interposed constitute a sensor cell 1*f*, and a current flows due to the decomposition of NOx at the electrode 164 confronting the second chamber 142. This current corresponds to the concentration of NOx in the second chamber 142.

Also in the gas sensor 1B thus constructed, the cell disconnection can be detected without receiving the influence of the other cells or the like in a manner such that a voltage variation is given between the cell electrodes to produce a current variation depending on a parasitic capacity between the electrodes.

In this case, although the voltage to be applied between the cell electrodes is changed, it is also appropriate to vary the current to be applied to a signal line.

Moreover, it is also appropriate that the disconnection detection is not always conducted periodically but the disconnection detection is made in a case in which a cell falls into a control-impossible condition or in a case in which an abnormal behavior appears in fuel injection control or the like using a detected gas concentration.

It should be understood that a present exemplary embodiment is not limited to the above-described embodiment, and that it is intended to cover all changes and modifications of the present exemplary embodiments herein which do not constitute departures from the spirit and scope of the present exemplary embodiments.

What is claimed is:

1. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:
    signal inputting processing mechanism for temporarily inputting a test signal including an alternating-current component through said signal line to said cell undergoing abnormality detection, said alternating-current component being above 1 kHz;
    response signal detector for detecting a response signal developing in said signal line in response to the inputting of said test signal; and
    decision processing mechanism for comparing a detection value of said response signal with a prescribed value and, if said detection value resides in one of regions defined by said prescribed value, making a decision that a disconnection abnormality occurs in said cell undergoing the abnormality detection.

2. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:
    signal inputting processing mechanism for temporarily inputting a test signal including an alternating-current component through said signal line to said cell undergoing abnormality detection;
    response signal detector for detecting a response signal developing in said signal line in response to the inputting of said test signal; and
    decision processing mechanism for comparing a detection value of said response signal with a prescribed value and, if said detection value resides in one of regions defined by said prescribed value, making a decision that a disconnection abnormality occurs in said cell undergoing the abnormality detection;
    wherein, for the detection of said response signal, a predetermined time delay is set with respect to said test signal.

3. A gas sensor abnormality detecting device made to detect the presence or absence of abnormality of a gas sensor composed of a plurality of cells each having a pair of electrodes formed on a solid electrolyte material to output a gas detection signal corresponding to a composition of a measured gas at surfaces of said electrodes through a signal line connected to the electrodes and made such that one electrodes of said pairs of electrodes of said plurality of cells are placed to confront a common chamber, said device comprising:
    test signal inputting processing mechanism for temporarily inputting a test signal including an alternating-current component through the signal lines to a specified cell of said plurality of cells, said alternating-current component being above 1 kHz;
    response signal detector for, in response to the inputting of said test signal, detecting a response signal developing in said signal line for a cell, undergoing abnormality detection, other than said specified cell; and
    decision processing mechanism for comparing a detection value of said response signal with a prescribed value and, if said detection value resides in preset one of regions defined by said prescribed value, making a decision that a disconnection abnormality occurs in said cell undergoing the abnormality detection.

4. A gas sensor abnormality detecting device made to detect the presence or absence of abnormality of a gas sensor composed of a plurality of cells each having a pair of electrodes formed on a solid electrolyte material to output a gas detection signal corresponding to a composition of a measured gas at surfaces of said electrodes through a signal line connected to the electrodes and made such that one electrodes of said pairs of electrodes of said plurality of cells are placed to confront a common chamber, said device comprising:
    test signal inputting Processing mechanism for temporarily inputting a test signal including an alternating-current component through the signal lines to a specified cell of said plurality of cells;
    response signal detector for, in response to the inputting of said test signal, detecting a response signal developing in said signal line for a cell, undergoing abnormality detection, other than said specified cell;
    decision processing mechanism for comparing a detection value of said response signal with a prescribed value and, if said detection value resides in preset one of regions defined by said prescribed value, making a decision that a disconnection abnormality occurs in said cell undergoing the abnormality detection; and
    second response signal detector for, in response to said test signal with respect to said specified cell, detecting a response signal developing in a signal line for said specified cell; and
    second decision processing mechanism for comparing a detection value of said response signal with a prescribed value to, if the detection value resides in preset one of the regions defined by said prescribed value, make a decision that a disconnection abnormality occurs in said specified cell.

5. The device according to claim 4, further comprising:
    response signal detector for, in response to the inputting of said test signal to said specified cell, detecting a response signal developing in a signal line for the specified cell;
    impedance calculator for obtaining an impedance between said electrodes of said specified cell on the basis of said test signal and said response signal; and
    heater controller for controlling a heater integrated with gas sensor together with the cell on the basis of the obtained impedance.

6. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:
    signal inputting processing mechanism for temporarily inputting a test signal including an alternating-current component through said signal line to said cell undergoing abnormality detection;
    response signal detector for detecting a response signal developing in said signal line in response to the inputting of said test signal;
    decision processing mechanism for comparing a detection value of said response signal with a prescribed value and, if said detection value resides in one of regions defined by said prescribed value, making a decision that a disconnection abnormality occurs in said cell undergoing the abnormality detection;

temperature state detector for detecting a temperature state of said solid electrolyte material; and inhibiting processing mechanism for inhibiting the abnormality decision processing in said decision processing mechanism until said temperature state reaches a predetermined temperature region of said solid electrolyte material.

7. The device according to claim 6, wherein said temperature state detector obtains an impedance between said electrodes on the basis of said test signal and said response signal, with said impedance being used as a parameter for said temperature state.

8. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:

signal inputting processing mechanism for temporarily inputting a test signal including an alternating-current component through said signal line to said cell undergoing abnormality detection;

response signal detector for detecting a response signal developing in said signal line in response to the inputting of said test signal; and decision processing mechanism for comparing a detection value of said response signal with a prescribed value and, if said detection value resides in one of regions defined by said prescribed value, making a decision that a disconnection abnormality occurs in said cell undergoing the abnormality detection;

wherein said test signal inputting processing mechanism inputs a temporary voltage variation as said test signal to said signal line, and said response signal detector detects a variation of a current flowing through said signal line as said response signal, and said decision processing mechanism sets, as said one region, a smaller region than said prescribed value and, when said detection value falls below said prescribed value, makes a decision that a disconnection abnormality occurs in said cell undergoing the abnormality detection.

9. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:

signal inputting processing mechanism for temporarily inputting a test signal including an alternating-current component through said signal line to said cell undergoing abnormality detection;

response signal detector for detecting a response signal developing in said signal line in response to the inputting of said test signal; and decision processing mechanism for comparing a detection value of said response signal with a prescribed value and, if said detection value resides in one of regions defined by said prescribed value, making a decision that a disconnection abnormality occurs in said cell undergoing the abnormality detection;

wherein said test signal inputting processing mechanism inputs a temporary current variation as said test signal to said signal line, and said response signal detector detects a variation of a voltage in said signal line as said response signal, and said decision processing mechanism sets, as the one region, a larger region than said prescribed value and, when said detection value exceeds said prescribed value, makes a decision that a disconnection abnormality occurs in said cell undergoing the abnormality detection.

10. A gas sensor abnormality detecting device made to detect the presence or absence of abnormality of a gas sensor composed of a cell having a pair of electrodes formed on a solid electrolyte material to output a gas detection signal corresponding to a composition of a measured gas on surfaces of said electrodes through a signal line connected to said electrodes, said device comprising:

test signal inputting processing mechanism for temporarily inputting a test signal including an alternating-current component through said signal line with respect to a cell undergoing abnormality detection, said alternating-current being above 1 kHz;

response signal detector for, in response to the inputting of said test signal, detecting a response signal developing in said signal line;

impedance calculator for obtaining an impedance between said electrodes on the basis of said test signal and said response signal; and decision processing mechanism for comparing the obtained impedance value with a prescribed value and, if the obtained impedance value exceeds said prescribed value, making a decision that a disconnection abnormality occurs in said undergoing abnormality detection.

11. A gas sensor abnormality detecting device made to detect the presence or absence of abnormality of a gas sensor composed of a cell having a pair of electrodes formed on a solid electrolyte material to output a gas detection signal corresponding to a composition of a measured gas on surfaces of said electrodes through a signal line connected to said electrodes, said device comprising:

test signal inputting processing mechanism for temporarily inputting a test signal including an alternating-current component through said signal line with respect to a cell undergoing abnormality detection;

response signal detector for, in response to the inputting of said test signal, detecting a response signal developing in said signal line;

impedance calculator for obtaining an impedance between said electrodes on the basis of said test signal and said response signal;

decision processing mechanism for comparing the obtained impedance value with a prescribed value and, if the obtained impedance value exceeds said prescribed value, making a decision that a disconnection abnormality occurs in said undergoing abnormality detection;

temperature state detector for detecting a temperature state of said solid electrolyte material; and inhibiting processing mechanism for inhibiting the abnormality decision processing in said decision processing mechanism until said temperature state reaches a predetermined temperature region of said solid electrolyte material.

12. The device according to claim 11, wherein said temperature state detector obtains an energizing time with respect to a heater integrated with said gas sensor together with said cell, with said energizing time being used as a parameter for said temperature state.

13. The device according to claim 11, wherein said temperature state detector obtains a total applied electric energy to a heater integrated with said gas sensor together with said cell, with said total applied electric energy being used as a parameter for said temperature state.

14. A gas sensor abnormality detecting device made to detect the presence or absence of abnormality of a gas sensor having a cell in which a pair of electrodes are formed on a solid electrolyte material to output a signal corresponding to a composition of a measured gas on surfaces of said electrodes through a signal line connected to said electrodes, said device comprising:

signal inputting processing mechanism for temporarily inputting a test signal including an alternating-current component through said signal line to said cell undergoing abnormality detection;

response signal detector for detecting a response signal developing in said signal line in response to the inputting of said test signal; and decision processing mechanism for comparing a detection value or said response signal with a prescribed value and, if said detection value resides in one of regions defined by said prescribed value, making a decision that a disconnection abnormality occurs in said cell undergoing the abnormality detection;

wherein said test signal inputting processing mechanism constitutes a power supply of said cell and temporarily inputs one of a voltage variation and a current variation to said signal line, and said response signal detector detects one of a variation of a current flowing through said signal line and a variation of a voltage between said electrodes as said response signal.

15. The device according to claim 14, wherein said test signal inputting processing mechanism inputs one of a voltage and a current varying in both a positive and negative directions with respect to one of a voltage and a current immediately before.

16. The device according to claim 14, wherein said test signal inputting processing mechanism inputs one of a voltage and a current varying in one of a positive and negative directions with respect to one of a voltage and a current immediately before.

* * * * *